(12) United States Patent
Steffens

(10) Patent No.: US 10,065,752 B2
(45) Date of Patent: Sep. 4, 2018

(54) VACUUM PACKING METHODS AND APPARATUS FOR TOBACCO

(71) Applicant: Alliance One International, Inc., Morrisville, NC (US)

(72) Inventor: Marcos Andre Steffens, Singapore (SG)

(73) Assignee: Alliance One International, Inc., Morrisville, NC (US)

( * ) Notice: Subject to any disclaimer, the term of this patent is extended or adjusted under 35 U.S.C. 154(b) by 681 days.

(21) Appl. No.: 13/758,399

(22) Filed: Feb. 4, 2013

(65) Prior Publication Data

US 2013/0227915 A1 Sep. 5, 2013

Related U.S. Application Data

(62) Division of application No. 13/441,373, filed on Apr. 6, 2012, now abandoned.

(Continued)

(51) Int. Cl.
*B65B 1/26* (2006.01)
*B65B 31/04* (2006.01)
(Continued)

(52) U.S. Cl.
CPC .............. *B65B 1/26* (2013.01); *A24F 23/00* (2013.01); *B65B 29/00* (2013.01); *B65B 31/00* (2013.01);
(Continued)

(58) Field of Classification Search
CPC  B65D 31/04; B65D 81/2038; B65D 85/1018; B65D 85/1072; A24F 23/02
(Continued)

(56) References Cited

U.S. PATENT DOCUMENTS 2,071,300 A * 2/1937 Gammeter ............ B65B 25/067
 206/497
2,364,012 A * 11/1944 Walton .................... B65D 5/60
 206/524.8

(Continued)

FOREIGN PATENT DOCUMENTS

CN 1748142 A 3/2006

OTHER PUBLICATIONS

Extended European Search Report, EP 12841786.2, dated Sep. 30, 2015, 12 pages.

(Continued)

*Primary Examiner* — Andrew M Tecco
*Assistant Examiner* — Chinyere Rushing-Tucker
(74) *Attorney, Agent, or Firm* — Myers Bigel, P.A.

(57) ABSTRACT

Apparatus and methods of packing leaf tobacco preserve the integrity of tobacco, help retain freshness and moisture content of tobacco, and also help eliminate insect infestation. A method of packing tobacco includes supplying a quantity of tobacco into a plurality of open containers; closing the opening containers; inserting the closed containers within a flexible, non-porous bag having a closeable opening; closing the opening of the bag; and extracting air from the bag so as to create a sub-atmospheric pressure therein. The bag is configured to hold one or more tobacco containers, such as C48 or A48 cartons. In some embodiments the bag may be configured to hold up to six containers, such as C48 or A48 cartons.

11 Claims, 27 Drawing Sheets

Related U.S. Application Data

(60) Provisional application No. 61/549,549, filed on Oct. 20, 2011.

(51) Int. Cl.
| | |
|---|---|
| *B65D 77/06* | (2006.01) |
| *B65D 81/20* | (2006.01) |
| *B65D 85/10* | (2006.01) |
| *A24F 23/00* | (2006.01) |
| *B65B 29/00* | (2006.01) |
| *B65B 31/00* | (2006.01) |
| *B65B 61/20* | (2006.01) |
| *G01N 31/22* | (2006.01) |

(52) U.S. Cl.
CPC .............. *B65B 31/04* (2013.01); *B65B 61/20* (2013.01); *B65D 77/062* (2013.01); *B65D 81/203* (2013.01); *B65D 81/2038* (2013.01); *B65D 85/10* (2013.01); *G01N 31/229* (2013.01); *G01N 31/222* (2013.01)

(58) Field of Classification Search
USPC .......................................... 53/405; 206/459.1
See application file for complete search history.

(56) References Cited

U.S. PATENT DOCUMENTS

| | | | |
|---|---|---|---|
| 3,641,734 A | 2/1972 | Fishburne | |
| 3,834,299 A * | 9/1974 | Bourgeois | B30B 9/3003 100/229 A |
| 4,457,125 A | 7/1984 | Fishburne | |
| 4,461,184 A * | 7/1984 | Gandhi | G01N 1/2226 73/863.23 |
| 5,007,233 A | 4/1991 | Bose | |
| 5,130,433 A | 7/1992 | Albarella et al. | |
| 5,274,914 A | 1/1994 | Kitamura et al. | |
| 5,369,261 A * | 11/1994 | Shamir | G06K 19/06037 235/468 |
| 5,887,409 A | 3/1999 | Leal Pereira Da Silva et al. | |
| 6,298,858 B1 | 10/2001 | Coleman, III | A24B 3/08 131/276 |
| 6,428,748 B1 * | 8/2002 | Wallach | G01N 21/78 422/421 |
| 7,325,382 B2 * | 2/2008 | Nelson | A24C 5/06 53/148 |
| 7,739,857 B2 | 6/2010 | McLaughlin et al. | |
| 7,958,696 B2 | 6/2011 | McLaughlin et al. | |
| 2004/0050738 A1 * | 3/2004 | Molina | A61F 13/551 206/440 |
| 2004/0159658 A1 * | 8/2004 | McLaughlin | B65B 27/125 220/4.21 |
| 2005/0043515 A1 * | 2/2005 | Brown | C07K 16/16 530/387.1 |
| 2005/0155891 A1 * | 7/2005 | Chen | B65D 5/3628 206/524.8 |
| 2005/0284775 A1 * | 12/2005 | McLaughlin | A01F 25/14 206/83.5 |
| 2007/0172910 A1 * | 7/2007 | Nolen | B65D 79/02 435/34 |
| 2008/0213445 A1 * | 9/2008 | Feinberg | A47J 37/1223 426/417 |
| 2008/0237239 A1 * | 10/2008 | Pham | B65D 77/062 220/495.06 |
| 2008/0307755 A1 * | 12/2008 | Stelliferi | B65B 31/00 53/469 |
| 2010/0068755 A1 * | 3/2010 | Walsh | C12Q 1/04 435/34 |
| 2010/0083615 A1 | 4/2010 | Till | |
| 2010/0190658 A1 * | 7/2010 | Van Der Eycken | G01N 33/52 506/9 |
| 2010/0242972 A1 | 9/2010 | Thierig et al. | |
| 2010/0276325 A1 * | 11/2010 | Sakurai | B65D 79/02 206/459.1 |
| 2011/0139655 A1 * | 6/2011 | Cochran | B65D 79/02 206/459.1 |
| 2011/0197549 A1 | 8/2011 | Share et al. | |
| 2011/0203228 A1 | 8/2011 | McLaughlin et al. | |
| 2011/0232232 A1 | 9/2011 | Rinehart et al. | |
| 2011/0259086 A1 * | 10/2011 | Harris | G01M 3/042 73/40.7 |
| 2012/0107191 A1 * | 5/2012 | Strahle | G01N 21/78 422/401 |

OTHER PUBLICATIONS

Tobaccoreporter—"Inside the Box"—TR Staff Report; Sep. 2012; pp. 46-47.

\* cited by examiner

VACUUM PACKING METHODS AND APPARATUS FOR TOBACCO

RELATED APPLICATION

This application is a divisional application of pending U.S. patent application Ser. No. 13/441,373, filed Apr. 6, 2012, which claims the benefit of and priority to U.S. Provisional Patent Application No. 61/549,549 filed Oct. 20, 2011, the disclosures of which are incorporated herein by reference as if set forth in their entireties.

FIELD OF THE INVENTION

The present invention relates generally to tobacco and, more particularly, to tobacco packing.

BACKGROUND

Leaf or "strip" tobacco, as well as other types of tobacco, is conventionally packed in rectangular cartons for storage and shipping. These rectangular cartons are typically constructed of cardboard and have standardized sizes to reduce transportation and packing costs. An exemplary cardboard carton 10, also known as a "C48" carton, is illustrated in FIG. 1. The "C48" designation is derived from the fact that 48 of these cartons can be placed within a standard 20 foot shipping container.

Conventionally, vertically operating tobacco packing presses are used to fill containers, such as C48 cartons, with tobacco. Typically, an open C48 carton communicates at its top with an elongated, hollow, upright charger. The charger supports a column of tobacco extending upwardly from the carton. A vertically acting press ram having a press head is aligned above the charger so that the ram can be operated to force the press head downwardly through the charger to, or into, the carton. Alternatively, the tobacco packing press may press the tobacco into a compression chamber, from where it is further forced into the carton. With the press head raised, the tobacco is supplied into the top of the charger, for example by a conveyor positioned below the press head. The tobacco is supplied until the charger contains a predetermined quantity of loose uncompacted tobacco (e.g., strip, loose leaf, bundle, butted loose leaf, cut rag, etc.). The ram is then operated to force the press head downwardly through the charger and compress the entire quantity of tobacco into the carton. Exemplary packing presses are described in U.S. Pat. Nos. 3,641,734 and 4,457,125.

Unfortunately, conventional packing cartons may not adequately protect the tobacco therewithin from environmental and other exposures or from infestation by harmful pests that can damage or destroy the tobacco.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Apparatus and methods of packing leaf tobacco, according to embodiments of the present invention, preserve the integrity of tobacco, help retain freshness and moisture content of tobacco, and also help eliminate insect infestation. Embodiments of the present invention may be used with all types of tobacco including, but not limited to, Flue Cured Virginia (FCV) tobacco, Burley tobacco, Oriental tobacco, Sun Cured tobacco, Dark Fired tobacco, etc. Moreover, green tobacco may be packed in accordance with embodiments of the present invention. In addition, embodiments of the present invention may be used with tobacco in all forms including, but not limited to, strip, loose leaf, bundle, butted loose leaf, cut rag, etc.

According to some embodiments of the present invention, a packing container for tobacco includes a carton, and a flexible, non-porous bag located within the carton. In some embodiments, the carton is a rectangular cardboard container, such as a standard C48 or A48 carton. The bag includes a closeable opening through which the bag receives a quantity of tightly packed tobacco. The bag is configured to have air extracted therefrom and to maintain a sub-atmospheric pressure therein of, for example, between about 0.10 bar to about 0.80 bar.

In some embodiments of the present invention, a colorimetric detector is inserted within the bag before closing the opening of the bag. The colorimetric detector is positioned so as to be viewable through the closed bag or through a portion of the closed bag. The colorimetric detector is configured to change color when an environmental condition within the bag changes and/or when a chemical element associated with the tobacco within the bag changes. For example, the colorimetric detector may be configured to change color when a moisture level and/or temperature level within the bag is outside of a predetermined range. As another example, the colorimetric detector may be configured to change color when an oxygen level, nitrogen level, and/or carbon-dioxide level, for example, within the bag is outside of a predetermined range. Furthermore, the colorimetric detector may be configured to change color when a chemical element (e.g., nitrosamines, sugars, oils, etc.) level associated with the tobacco within the bag is outside of a predetermined range.

In some embodiments, the flexible, non-porous bag is formed from a multi-layered composite material with at least one of the layers being an aluminum layer. For example, in some embodiments, the multi-layered composite includes an aluminum layer sandwiched between first and second polymeric layers. In other embodiments, the bag is formed from a multi-layered composite having a polystyrene inner layer, an aluminum middle layer, and a nylon outer layer. In other embodiments, the bag is formed from a semi-transparent or opaque material, or is formed from a multi-layered composite having at least one layer being a semi-transparent or opaque material.

A flexible, non-porous bag according to some embodiments of the present invention may have a wall thickness of at least about 100 microns. In other embodiments, wall thickness may be between about 100 microns and about 200 microns.

According to some embodiments of the present invention, the bag opening is a re-sealable opening including a male zipper portion and a corresponding female zipper portion that is configured to matingly engage with the male zipper portion. A slide mechanism is movably secured to the bag opening and is configured to slide along the opening and facilitate engagement of the male and female zipper portions to close the bag.

According to some embodiments of the present invention, the bag includes a valve that is utilized for extracting air therefrom. The valve may also be utilized to purge the bag, when closed, for example with an inert gas prior to extracting air from the bag.

According to other embodiments of the present invention, a packing container for tobacco, comprises a flexible, non-porous bag having a closeable opening through which the bag receives a quantity of tightly packed tobacco. The bag is configured to have air extracted therefrom and to maintain a sub-atmospheric pressure therein, for example, of between about 0.10 bar to about 0.80 bar. In some embodiments, the bag is formed from an opaque or semi-transparent material. In some embodiments the bag is formed from a multi-layered composite material, and wherein at least one of the layers comprises aluminum. In some embodiments, the bag is formed from a multi-layered composite material, and wherein at least one of the layers is an opaque or semi-transparent material, or wherein at least one layer has a color that renders the layer opaque or semi-transparent.

In some embodiments, the bag has a tubular shape. In other embodiments, the bag has a generally rectangular or cubic shape.

In some embodiments of the present invention, a colorimetric detector is inserted within the bag before closing the opening of the bag. The colorimetric detector is positioned so as to be viewable through the closed bag or a portion of the bag. The colorimetric detector is configured to change color when an environmental condition within the bag changes and/or when a chemical element associated with the tobacco within the bag changes. For example, the colorimetric detector may be configured to change color when a moisture level, oxygen level, nitrogen level and/or carbon-dioxide level within the bag is outside of a predetermined range, as described above. Moreover, the colorimetric detector may be configured to change color when a chemical element (e.g., nitrosamines, sugars, oils, etc.) level associated with the tobacco within the bag is outside of a predetermined range.

According to some embodiments of the present invention, a method of packing tobacco includes supplying a quantity of tightly packed tobacco into a flexible, non-porous bag through a closeable opening thereof, wherein the bag is positioned within an open container; closing the opening of the bag; extracting air from the bag so as to create a sub-atmospheric pressure therein; and closing the open container such that the bag resides within the closed container. The step of supplying a quantity of tightly packed tobacco into the bag may include compressing the tobacco within the bag by forcing a press ram downwardly through the bag opening. In some embodiments, the closed bag is purged with an inert gas prior to extracting air from the bag.

According to some embodiments of the present invention, a method of packing tobacco includes supplying a quantity of tightly packed tobacco into a flexible, non-porous bag through a closeable opening thereof; closing the opening of the bag; and extracting air from the bag so as to create a sub-atmospheric pressure therein. The step of supplying a quantity of tightly packed tobacco into the bag may include compressing the tobacco within the bag by forcing a press ram downwardly through the bag opening. In some embodiments, the closed bag is purged with an inert gas prior to extracting air from the bag.

According to some embodiments of the present invention, a method of packing tobacco includes supplying a quantity of tightly packed tobacco into a plurality of flexible, non-porous bags through a respective closeable opening of each, wherein each bag is positioned within a respective open rectangular carton; closing the openings of the bags; extracting air from the bags so as to maintain a sub-atmospheric pressure therein; closing the open cartons such that each bag resides within a respective closed carton; and stacking the closed cartons. In some embodiments, the closed containers are stacked within a shipping container.

According to some embodiments of the present invention, a method of packing tobacco includes supplying a quantity of tightly packed tobacco into a plurality of flexible, non-porous bags through a respective closeable opening of each; closing the openings of the bags; extracting air from the bags so as to maintain a sub-atmospheric pressure therein; and stacking the closed bags. In some embodiments, the closed bags are stacked within a shipping container.

According to some embodiments of the present invention, a packing container for leaf tobacco, comprises a carton having a sealable opening through which the carton receives a quantity of tightly packed tobacco. The carton is configured to have air extracted therefrom and to maintain a sub-atmospheric pressure therein of, for example, between about 0.10 bar to about 0.80 bar. The carton includes a valve through which air is extracted from the carton. In some embodiments, the valve is a two-way valve to permit the carton to be purged with an inert gas prior to extracting air from the carton.

In some embodiments of the present invention, the carton includes a colorimetric detector that is viewable through a window in the carton. The colorimetric detector is configured to change color when an environmental condition within the carton changes and/or when a chemical element associated with the tobacco within the carton changes. For example, the colorimetric detector may be configured to change color when a moisture level within the carton is outside of a predetermined range. The colorimetric detector may be configured to change color when an oxygen level, nitrogen level and/or carbon-dioxide level within the carton is outside of a predetermined range. Furthermore, the colorimetric detector may be configured to change color when a chemical element (e.g., nitrosamines, sugars, oils, etc.) level associated with the tobacco within the carton is outside of a predetermined range.

According to some embodiments of the present invention, a method of packing tobacco includes supplying a quantity of tobacco into a plurality of open containers; closing the opening containers; inserting the closed containers within a flexible, non-porous bag having a closeable opening; closing the opening of the bag; and extracting air from the bag so as to create a sub-atmospheric pressure therein. The bag is configured to hold one or more tobacco containers, such as C48 or A48 cartons. In some embodiments the bag may be configured to hold up to six containers, such as C48 or A48 cartons.

The bag is configured to have air extracted therefrom and to maintain a sub-atmospheric pressure therein of, for example, between about 0.10 bar to about 0.80 bar. The flexible, non-porous bag may be formed from a multi-layered composite material with at least one of the layers being an aluminum layer. For example, in some embodiments, the multi-layered composite includes an aluminum layer sandwiched between first and second polymeric layers. In other embodiments, the bag is formed from a multi-layered composite having a polystyrene inner layer, an aluminum middle layer, and a nylon outer layer. In other embodiments, the bag is formed from a semi-transparent or opaque material, or is formed from a multi-layered composite having at least one layer being a semi-transparent or opaque material.

The flexible, non-porous bag may have a wall thickness of at least about 100 microns, and may have a wall thickness between about 100 microns and about 200 microns. In some embodiments, the bag opening is a re-sealable opening including a male zipper portion and a corresponding female zipper portion that is configured to matingly engage with the male zipper portion.

According to some embodiments of the present invention, the bag includes a valve that is utilized for extracting air therefrom. The valve may also be utilized to purge the bag, when closed, for example with an inert gas prior to extracting air from the bag.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

DETAILED DESCRIPTION

Figure 1:
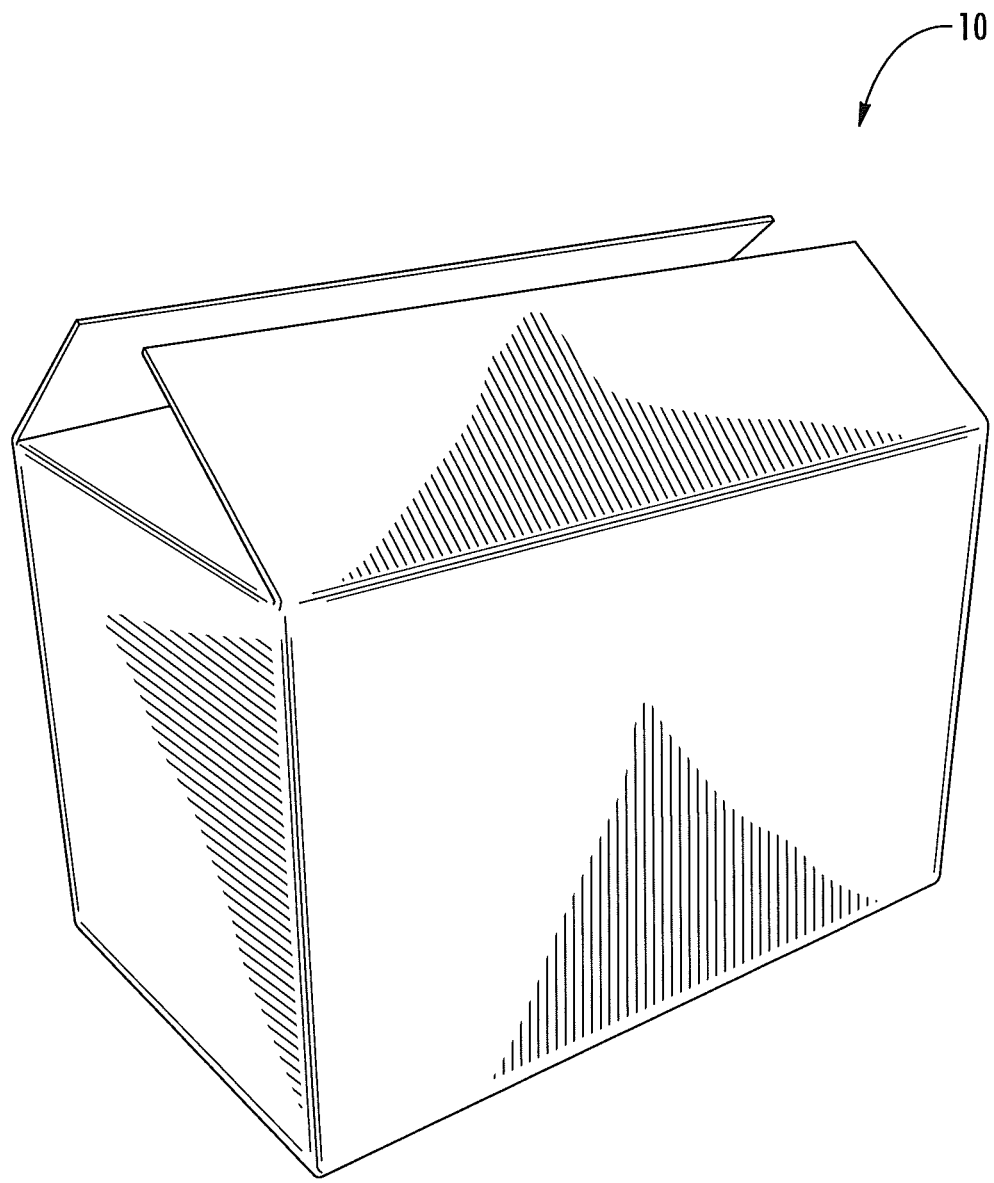
FIG. 1 is a perspective view of a conventional carton for storing and shipping tobacco.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain components or features may be exaggerated for clarity. In addition, the sequence of operations (or steps) is not limited to the order presented in the claims unless specifically indicated otherwise.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment and/or figure, the features and elements so described or shown can apply to other embodiments and/or figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/". As used herein, phrases such as "between X and Y" and "between about X and Y" should be interpreted to include X and Y. As used herein, phrases such as "between about X and Y" mean "between about X and about Y." As used herein, phrases such as "from about X to about Y" mean "from about X to about Y."

Spatially relative terms, such as "under", "below", "lower", "over", "upper" and the like, may be used herein for ease of description to describe one element or feature's relationship to another element(s) or feature(s) as illustrated in the Figures. It will be understood that the spatially relative terms are intended to encompass different orientations of the device in use or operation in addition to the orientation depicted in the Figures. For example, if a device in the Figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "tobacco", as used herein, includes any and all types of tobacco including, but not limited to, Flue Cured Virginia (FCV) tobacco, Burley tobacco, Oriental tobacco, Sun Cured tobacco, Dark Fired tobacco, green tobacco, and also includes tobacco in various forms including, but not limited to, strip, loose leaf, bundle, butted loose leaf, and cut rag.

Referring now to FIGS. 4-10, a packing container 20 and methods of packing tobacco in the packing container 20, according to some embodiments of the present invention, will be described. The illustrated packing container 20 includes a carton 10, such as a C48 style carton, A48 style carton (both of which are available from Jayaraj Fortune Packaging Private Limited, Andhra Pradesh, India), or other standardized size carton used in the tobacco industry, and a flexible, non-porous bag 30 located within the carton 10. Embodiments of the present invention are not limited to C48 or A48 cartons, or even to rectangular cartons. Various types and shapes of cartons and containers may be utilized to contain a flexible, non-porous bag 30 according to embodiments of the present invention. Moreover, C48 and A48 cartons are typically cardboard cartons. However, a packing container carton 10, according to embodiments of the present invention, can be formed from various materials, without limitation.

Figure 4:
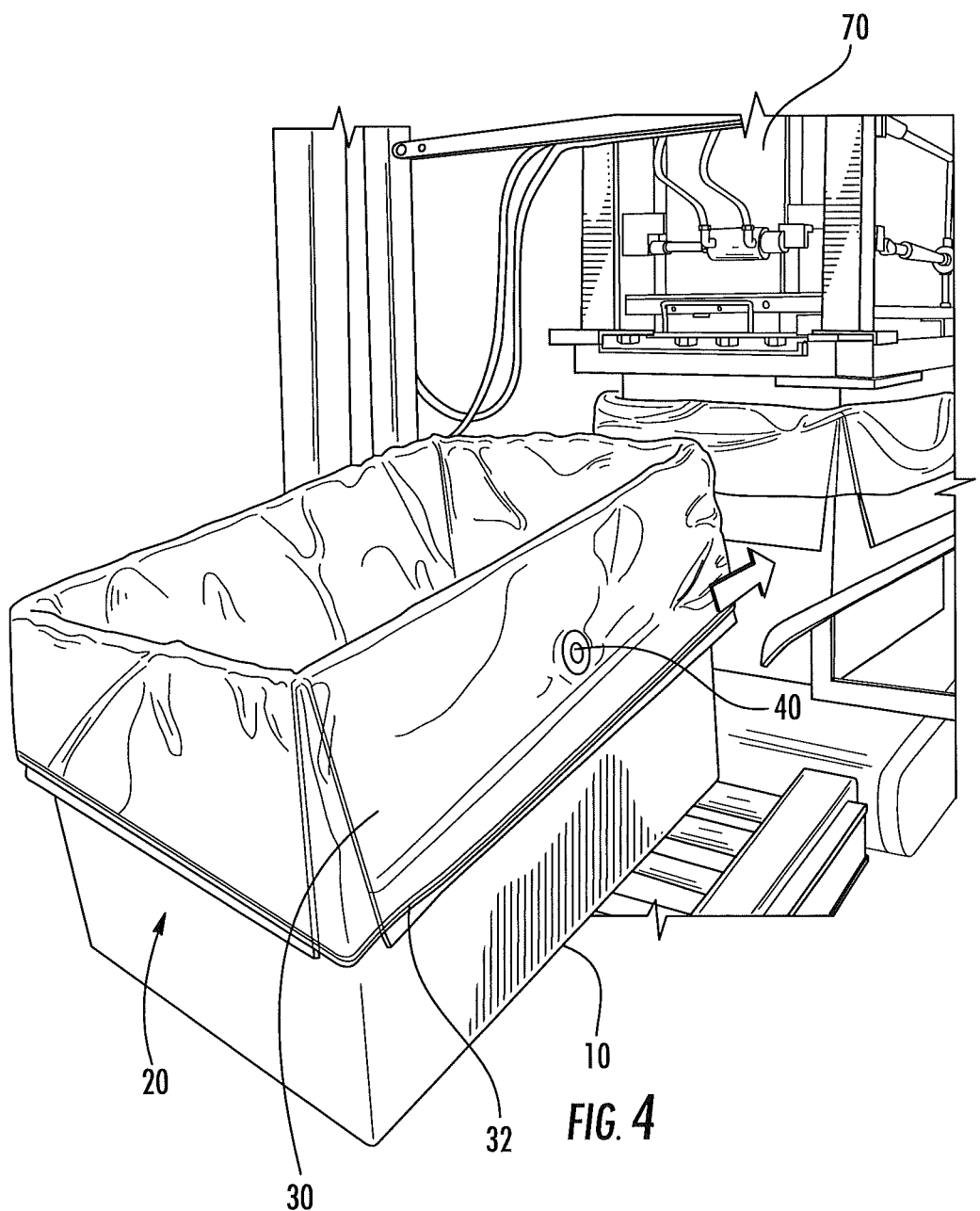
FIG. 4 illustrates packing containers, according to some embodiments of the present invention, on a conveyor for receiving a quantity of tightly packed tobacco from a packing press.
Figure 6:
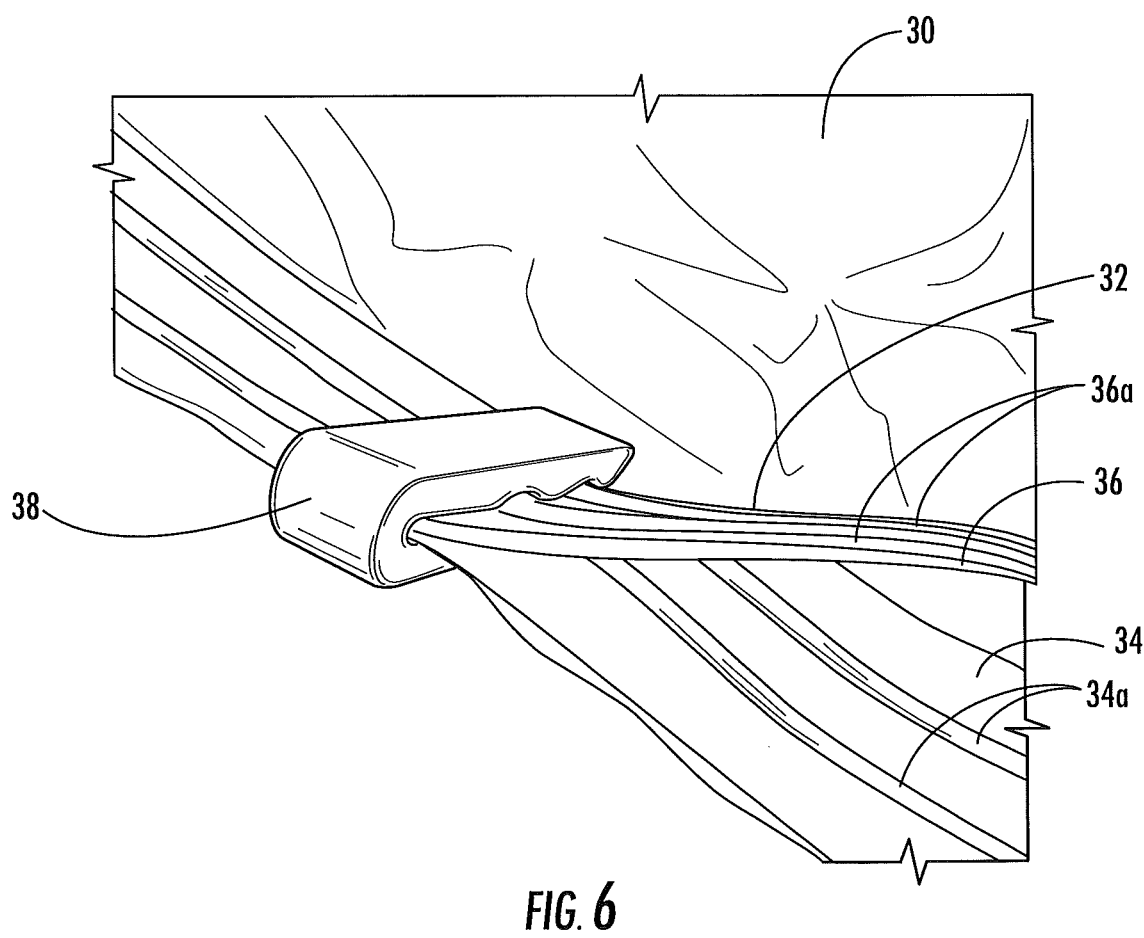
FIG. 6 is a partial perspective view of the closeable opening of the bag in the packing containers of FIG. 4 and a sliding mechanism that slides along the opening to facilitate engagement of the female and male zipper portions, according to some embodiments of the present invention.

The illustrated non-porous bag 30 includes a closeable opening 32 through which the bag 30 receives a quantity of tobacco, for example, tightly packed tobacco from a packing press (70, FIG. 4). The closeable opening 32 is large enough to allow tobacco packing press equipment to be inserted within a bag 30 to supply a quantity of tobacco. In the illustrated embodiment, the bag opening 32 is a re-sealable opening that includes a male zipper portion 34 and a corresponding female zipper portion 36 that is configured to matingly engage with the male zipper portion 34 (FIG. 6). The male zipper portion 34 includes a plurality of elongated ribs 34a that are configured to releasably engage respective elongated channels 36a in the female zipper portion 36. A slide mechanism 38 (FIG. 6) is movably secured to the bag opening 32 and is configured to slide along the bag opening 32 to facilitate engagement of the male and female zipper portions 34, 36 in order to close the bag opening 32 after the bag 30 has been supplied with a quantity of tobacco. In operation, a user moves the slide mechanism 38 back and forth along the opening 32 one or more time to ensure that the elongated ribs 34a are completely engaged within the elongated channels 36a such that the bag 30 is sealed closed. The bag opening 32 is configured to withstand numerous openings and closings without losing integrity.

Embodiments of the present invention are not limited to the configuration of the illustrated bag opening 32 or to the illustrated configuration of the male and female zipper portions 34, 36. Moreover, embodiments of the present invention are not limited to zipper-type openings. Various types of re-sealable openings may be utilized in accordance with embodiments of the present invention, without limitation. In addition, non-resealable openings may be utilized. For example, in some embodiments of the present invention, a bag opening 32 may be heat sealed.

Figures 7A, 7B:
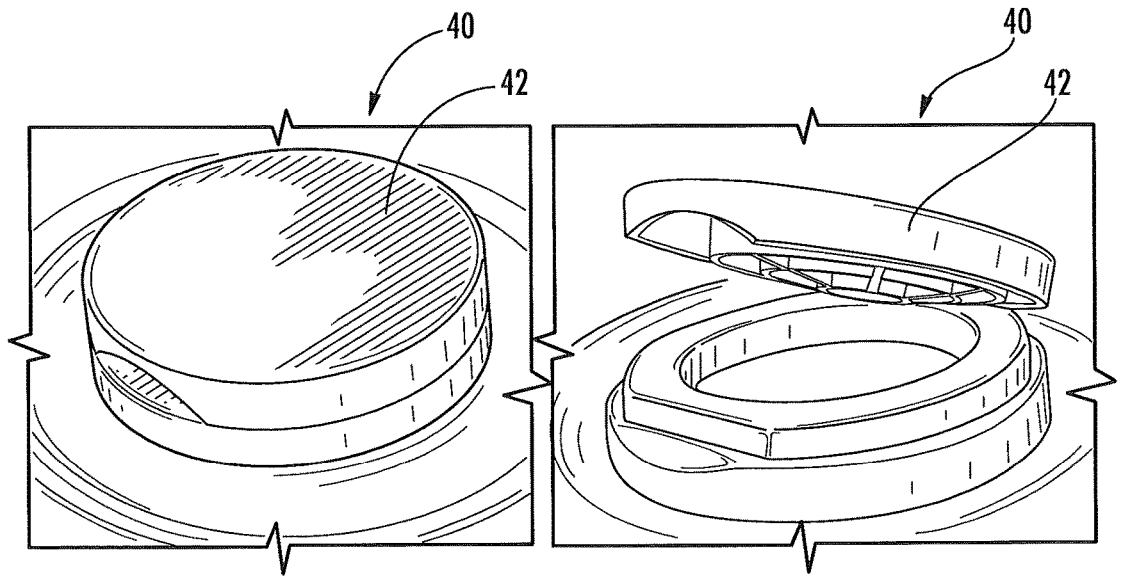
FIG. 7A is an enlarged perspective view of a valve for extracting air from the flexible, non-porous bag of FIG. 5, according to some embodiments of the present invention.
FIG. 7B is an enlarged perspective view of the valve of FIG. 7A with the cap thereof being moved to an open position.
Figure 7C:
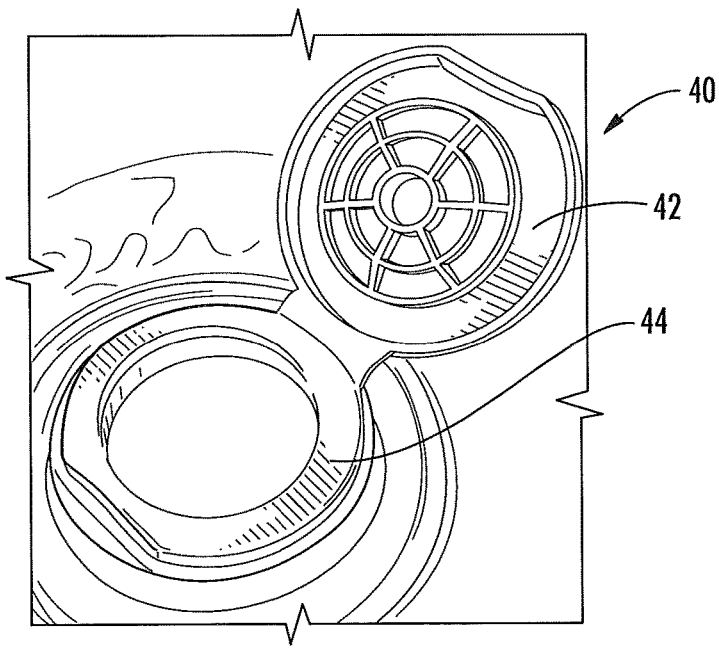
FIG. 7C is an enlarged perspective view of the valve of FIG. 7A with the cap thereof in the open position.
Figure 7D:
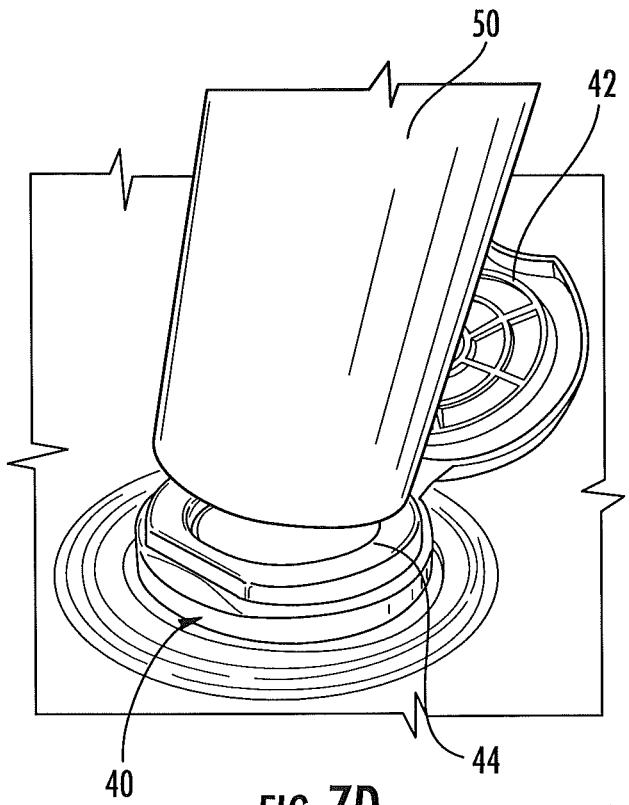
FIG. 7D is an enlarged perspective view of a vacuum tube about to engage the valve of FIG. 7C for extracting air from the bag, according to some embodiments of the present invention.
Figure 7E:
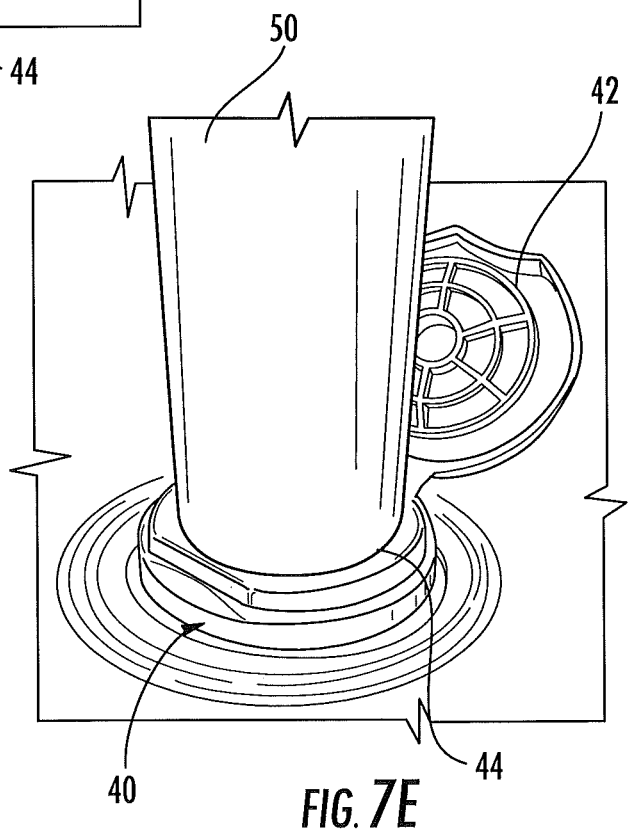
FIG. 7E illustrates the vacuum tube of FIG. 7D in a seated position over the mouth of the open valve of FIG. 7C.

The illustrated bag 30 also includes a valve 40 (FIG. 4) that is utilized for extracting air from the bag 30 after receiving tobacco therein and after the bag opening 32 is sealed closed. The valve 40 may be a two-way valve to allow the bag 30 to be purged with an inert gas (e.g., nitrogen, etc.) prior to being used to extract air from the bag 30. Referring to FIGS. 7A-7E, the illustrated valve 40 includes a cap 42 that is movable between closed (FIG. 7A) and open positions (FIG. 7C). When the cap 42 is in the open position, a vacuum tube 50 (FIGS. 7D, 7E) can engage the mouth 44 of the valve 40 and extract air from within the bag 30, as would be understood by those skilled in the art. Embodiments of the present invention are not limited to a particular type of valve 40. Various types and shapes of valves may be utilized in accordance with embodiments of the present invention. in some embodiments, valve 40 is a one-way valve that only permits extraction of air from a bag 30.

Figure 2:
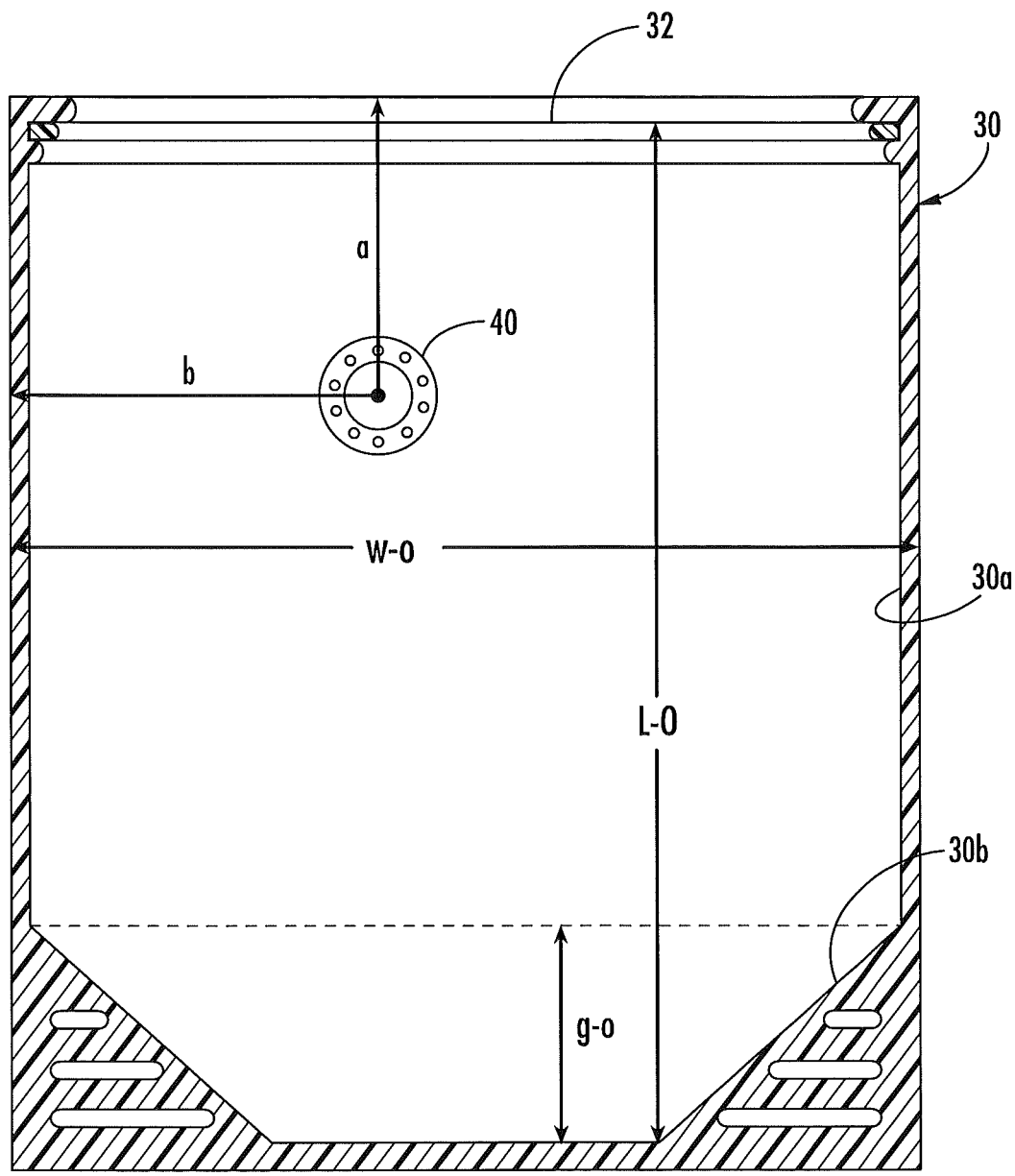
FIG. 2 is a cross sectional view of a flexible, non-porous bag for receiving tobacco therein, according to some embodiments of the present invention.

FIG. 2 is a cross-sectional view illustrating various dimensions of an exemplary flexible, non-porous bag 30 for packing containers 20, according to some embodiments of the present invention. The illustrated bag 30 has an internal length, indicated by "L-O", and an internal width, indicated by "W-O". an exemplary dimension for "L-O" is about 130 cm and an exemplary dimension for "W-O" is about 200 cm. The interior volume 30a has a tapered bottom portion 30b, as illustrated. The tapered bottom portion 30b has a length, indicated by "g-o". An exemplary dimension for "g-o" is about 74 cm. However, other dimensions may be utilized for "W-O", "L-O", and "g-o". Embodiments of the present invention are not limited to these particular dimensions.

The valve 40 is located a distance "a" from the top of the bag, and is located a distance "b" from the side of the bag, as illustrated. An exemplary dimension "a" is about 20 cm and an exemplary dimension "b" is about 100 cm. However, other dimensions may be utilized for "a" and "b". Embodiments of the present invention are not limited to these particular dimensions.

Bags 30 (and 130, FIGS. 11-13), according to embodiments of the present invention, are not limited to the illustrated configuration and dimensions of FIG. 2. Bags of various external and internal shapes and configurations may be utilized, without limitation. For example, as described below with respect to FIGS. 21-26, a bag may have a tubular shape. Moreover, a valve 40 may be located in various locations on a bag 30, 130, 330 (FIG. 26).

Flexible, non-porous bags 30 (and 130, FIGS. 11-13, and 330, FIGS. 21-26), according to embodiments of the present invention, are formed from material sufficient to maintain a sub-atmospheric pressure therein of between about 0.10 bar to about 0.80 bar for an indefinite period time and to also support the weight of the tobacco therein. Bags 30, 130, 330 according to embodiments of the present invention may be configured to maintain a sub-atmospheric pressure therein anywhere within the range of about 0.10 bar to about 0.80 bar (e.g., 0.10 bar, 0.11 bar, 0.12 bar, 0.13 bar, 0.14 bar, 0.15 bar, 0.16 bar, 0.17 bar, 0.18 bar, 0.19 bar, 0.20 bar, 0.21 bar, 0.22 bar, 0.23 bar, 0.24 bar, 0.25 bar, 0.26 bar, 0.27 bar, 0.28 bar, 0.29 bar, 0.30 bar, 0.31 bar, 0.32 bar, 0.33 bar, 0.34 bar, 0.35 bar, 0.36 bar, 0.37 bar, 0.38 bar, 0.39 bar, 0.40 bar, 0.41 bar, 0.42 bar, 0.43 bar, 0.44 bar, 0.45 bar, 0.46 bar, 0.47 bar, 0.48 bar, 0.49 bar, 0.50 bar, 0.51 bar, 0.52 bar, 0.53 bar, 0.54 bar, 0.55 bar, 0.56 bar, 0.57 bar, 0.58 bar, 0.59 bar, 0.60 bar, 0.61 bar, 0.62 bar, 0.63 bar, 0.64 bar, 0.65 bar, 0.66 bar, 0.67 bar, 0.68 bar, 0.69 bar, 0.70 bar, 0.71 bar, 0.72 bar, 0.73 bar, 0.74 bar, 0.75 bar, 0.76 bar, 0.77 bar, 0.78 bar, 0.79 bar, 0.80 bar, etc. Moreover, bags 30 (and 130, FIGS. 11-13, and 330, FIGS. 21-26) according to embodiments of the present invention can be configured to maintain a sub-atmospheric pressure therein in any range within the range of 0.10 bar to 0.80 bar (e.g., 0.10 bar to 0.20 bar; 0.20 bar to 0.30 bar; 0.30 bar to 0.40 bar; 0.40 bar to 0.50 bar; 0.50 bar to 0.60 bar; 0.60 bar to 0.70 bar; 0.70 bar to 0.80 bar; etc.).

Sub-atmospheric pressure may be varied in order to control aging and/or fermentation of tobacco stored within bags 30 (and 130, FIGS. 11-13, and 330, FIGS. 21-26), according to embodiments of the present invention. For example, some customers may desire a certain aging rate and/or fermentation of tobacco within a bag 30, 130, 330 which can be controlled via the sub-atmospheric pressure within the bag 30, 130, 330.

In some situations, a packing container 20 filled with tobacco in accordance with embodiments of the present invention may be stored for years. The internal bag 30 is designed to maintain the desired sub-atmospheric pressure for the entire length of the storage. The non-porous characteristic of the bag material prohibits insects and other pests from detecting the presence of tobacco within the bag 30 because no smell (e.g., tobacco odor) can escape from the bag 30.

An exemplary wall thickness of flexible, non-porous material for use in bags 30, according to embodiments of the present invention, is about 100 microns. However, material with different wall thicknesses, higher or lower than 100 microns, may be utilized. In some embodiments, a wall thickness of flexible, non-porous material for use in bags 30 may be between about 100 microns and about 200 microns. However, any size within this range may be utilized e.g., 101 microns, 102 microns, 103 microns, 104 microns, 105 microns, 106 microns, 107 microns, 108 microns, 109 microns, 110 microns, 111 microns, 112 microns, 113 microns, 114 microns, 115 microns, 116 microns, 117 microns, 118 microns, 119 microns, 120 microns, 121 microns, 122 microns, 123 microns, 124 microns, 125 microns, 126 microns, 127 microns, 128 microns, 129 microns, 130 microns, 131 microns, 132 microns, 133 microns, 134 microns, 135 microns, 136 microns, 137 microns, 138 microns, 139 microns, 140 microns, 141 microns, 142 microns, 143 microns, 144 microns, 145 microns, 146 microns, 147 microns, 148 microns, 149 microns, 150 microns, 151 microns, 152 microns, 153 microns, 154 microns, 155 microns, 156 microns, 157 microns, 158 microns, 159 microns, 160 microns, 161 microns, 162 microns, 163 microns, 164 microns, 165 microns, 166 microns, 167 microns, 168 microns, 169 microns, 170 microns, 171 microns, 172 microns, 173 microns, 174 microns, 175 microns, 176 microns, 177 microns, 178 microns, 179 microns, 180 microns, 181 microns, 182 microns, 183 microns, 184 microns, 185 microns, 186 microns, 187 microns, 188 microns, 189 microns, 190 microns, 191 microns, 192 microns, 193 microns, 194 microns, 195 microns, 196 microns, 197 microns, 198 microns, 199 microns, 200 microns, etc.

Figure 3A:
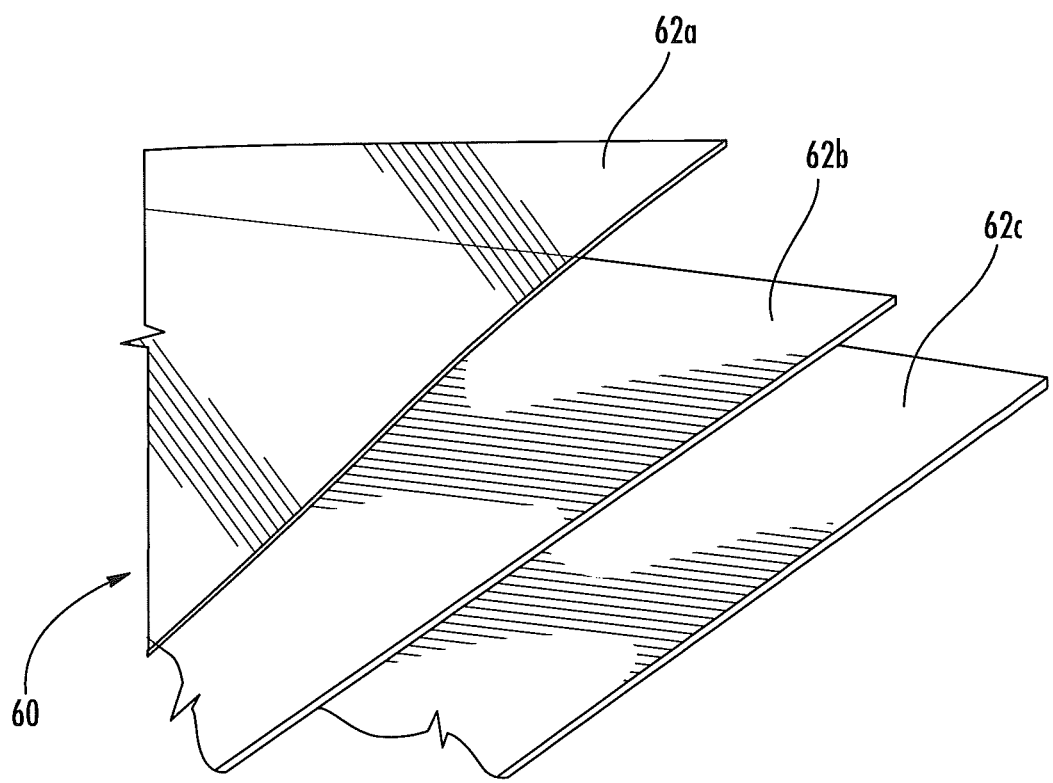
FIG. 3A is an enlarged, exploded view of a multi-layered composite material out of which a flexible, non-porous bag for receiving tobacco therein is formed, according to some embodiments of the present invention.

In addition, bags 30 according to embodiments of the present invention may be formed from a single layer of material or from a multi-layered composite material (e.g., 3 layers, 4 layers, 5 layers, 7 layers or more). FIG. 3A illustrates an exemplary three layer material 60 wherein the first layer 62a is nylon, the middle layer 62b is aluminum, and the third layer 62c is polystyrene. However, various polymeric materials may be utilized for the first and third layers 62a, 62c. Embodiments of the present invention are not limited to multi-layered composites utilizing only nylon and polystyrene. In addition, embodiments of the present invention are not limited to multi-layered composites utilizing an aluminum layer. Other layers of metallic, non transparent material may be utilized in accordance with embodiments of the present invention.

Bags 30 according to embodiments of the present invention do not require a metallic material. According to other embodiments of the present invention, an internal bag 30 may be formed from an opaque or semi-transparent material, or may be formed from a multi-layered composite having at least one layer being an opaque or semi-transparent material.

In other embodiments of the present invention, the layers 62a, 62b, 62c of bag 30 in FIG. 3A can be formed from polymeric material with at least one of the layers being opaque or semi-transparent. For example, one of the layers can be formed from opaque or semi-transparent material or can have a color (e.g., blue, black, etc.) that renders the layer opaque or semi-transparent.

Figure 3B:
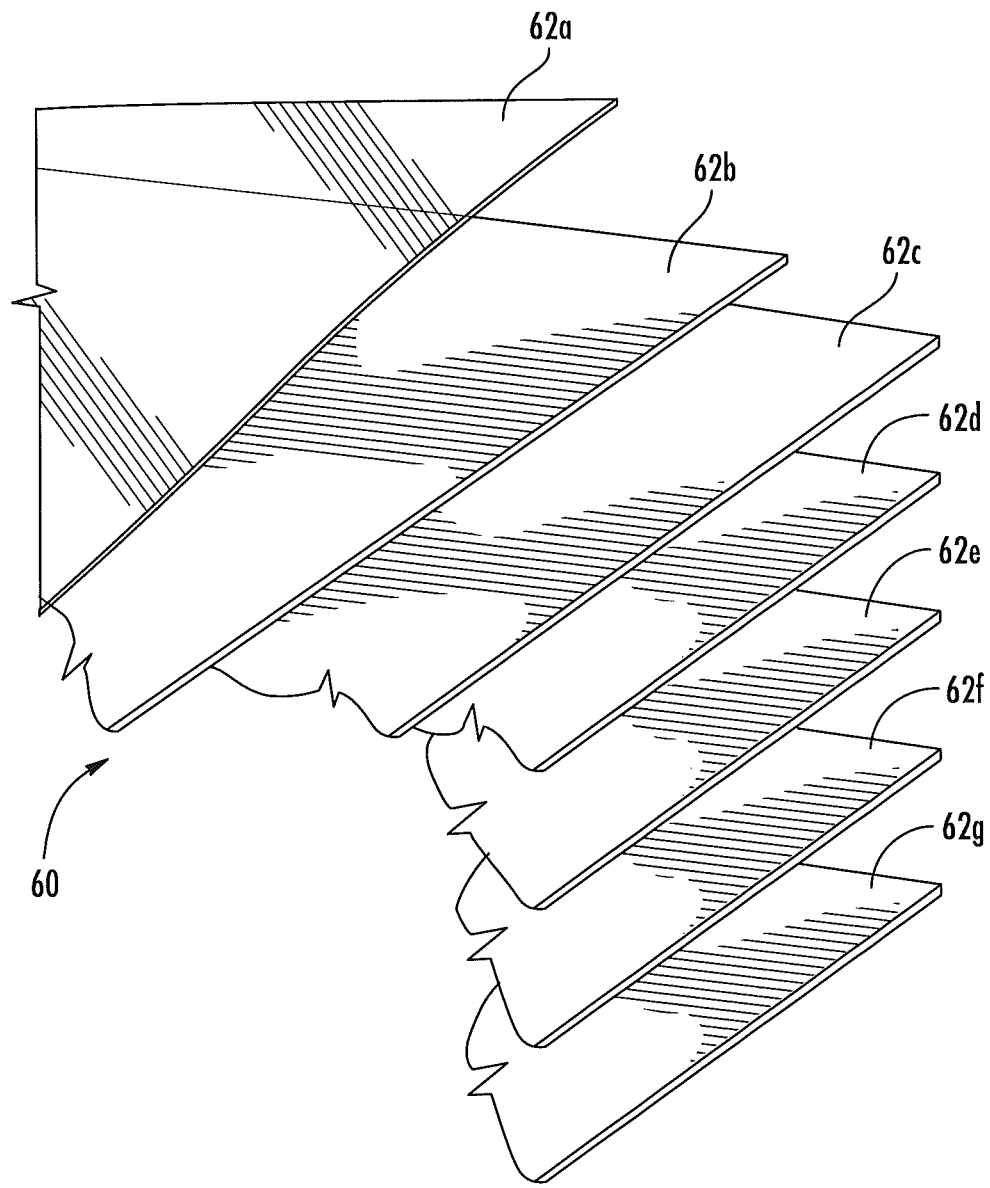
FIG. 3B is an enlarged, exploded view of a multi-layered composite material out of which a flexible, non-porous bag for receiving tobacco therein is formed, according to some embodiments of the present invention.

FIG. 3B illustrates an exemplary seven layer material 60 for an internal bag 30 having layers 62a-62g. Each of the layers (i.e., 62a, 62b, 62c, 62d, 62e, 62f, 62g) can be a polymeric material. In some embodiments of the present invention, at least one of the layers is formed from an opaque or semi-transparent material. In some embodiments of the present invention, at least one of the layers has a color that renders the layer opaque or semi-transparent.

The thickness of individual layers in a multi-layer composite (FIGS. 3A and 3B), according to embodiments of the present invention, may be different depending on the type of material used. For example, in the illustrated embodiment of FIG. 3A, the nylon layer 62a may have a thickness of about 15 microns, the aluminum layer 62b may have a thickness of about 25 microns, and the polystyrene layer 62c may have a thickness of about 60 microns.

Referring back to FIG. 4, a packing container 20 according to some embodiments of the present invention is positioned beneath a tobacco packing press 70 for receiving a quantity of tightly packed tobacco 80. After the packing container 20 receives the tobacco 80 within the internal bag 30, the packing container 20 is moved along a conveyor to a closing station (not shown) and the next packing container 20 is moved into position beneath the tobacco packing press 70. At the closing station, the bag opening 32 is closed and air is extracted from within the bag 30, as described above. In some embodiments of the present invention, the tobacco 80 may be subjected to a blanket of inert gas prior to evacuating the air therefrom. The inert gas may help kill any pests or organisms (e.g., insects, bacteria, fungi, etc.) present in the tobacco 80 and may help reduce the oxygen concentration in any remaining air within the bag 30 after a sub-atmospheric pressure has been induced therewithin.

Figure 5:
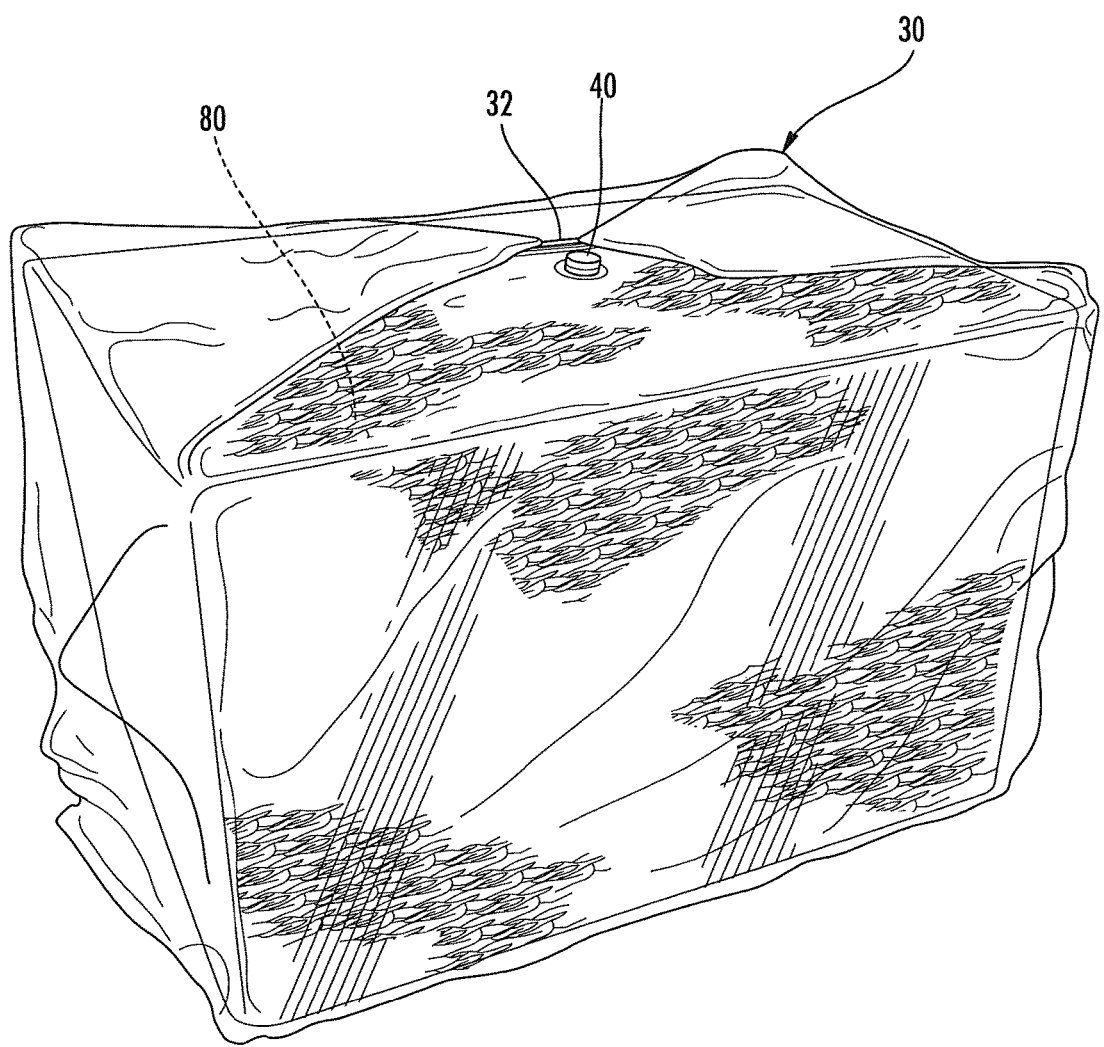
FIG. 5 is a perspective view of a flexible, non-porous bag of one of the packing containers of FIG. 4 after receiving a quantity of tightly packed tobacco therewithin, after the bag opening has been closed, and with the filled bag removed from the carton. The carton is not shown to illustrate that the tobacco is tightly packed.
Figure 8:
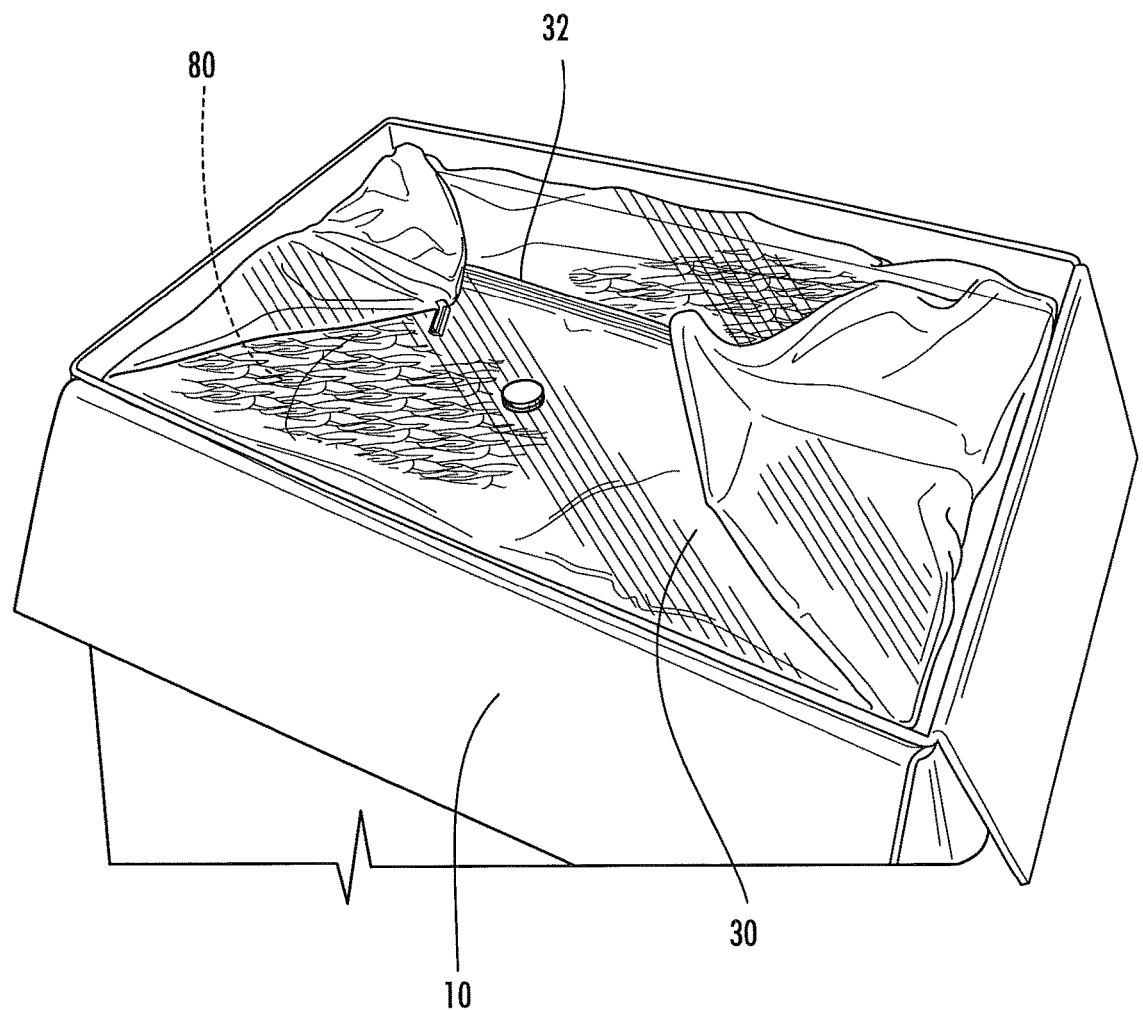
FIG. 8 is a perspective view of a packing container that includes a carton and a flexible bag therein, according to embodiments of the present invention, with a quantity of tobacco within the bag, and after the bag opening has been closed.

FIG. 5 illustrates a closed bag 30 from a packing container 20 according to some embodiments of the present invention and having a quantity of tightly packed tobacco 80 disposed therewithin. The carton 10 is not illustrated so that the amount of packing of the tobacco within the bag 30 can be observed. FIG. 8 illustrates the closed bag 30 of FIG. 5 positioned within an open carton 10.

Figure 9A:
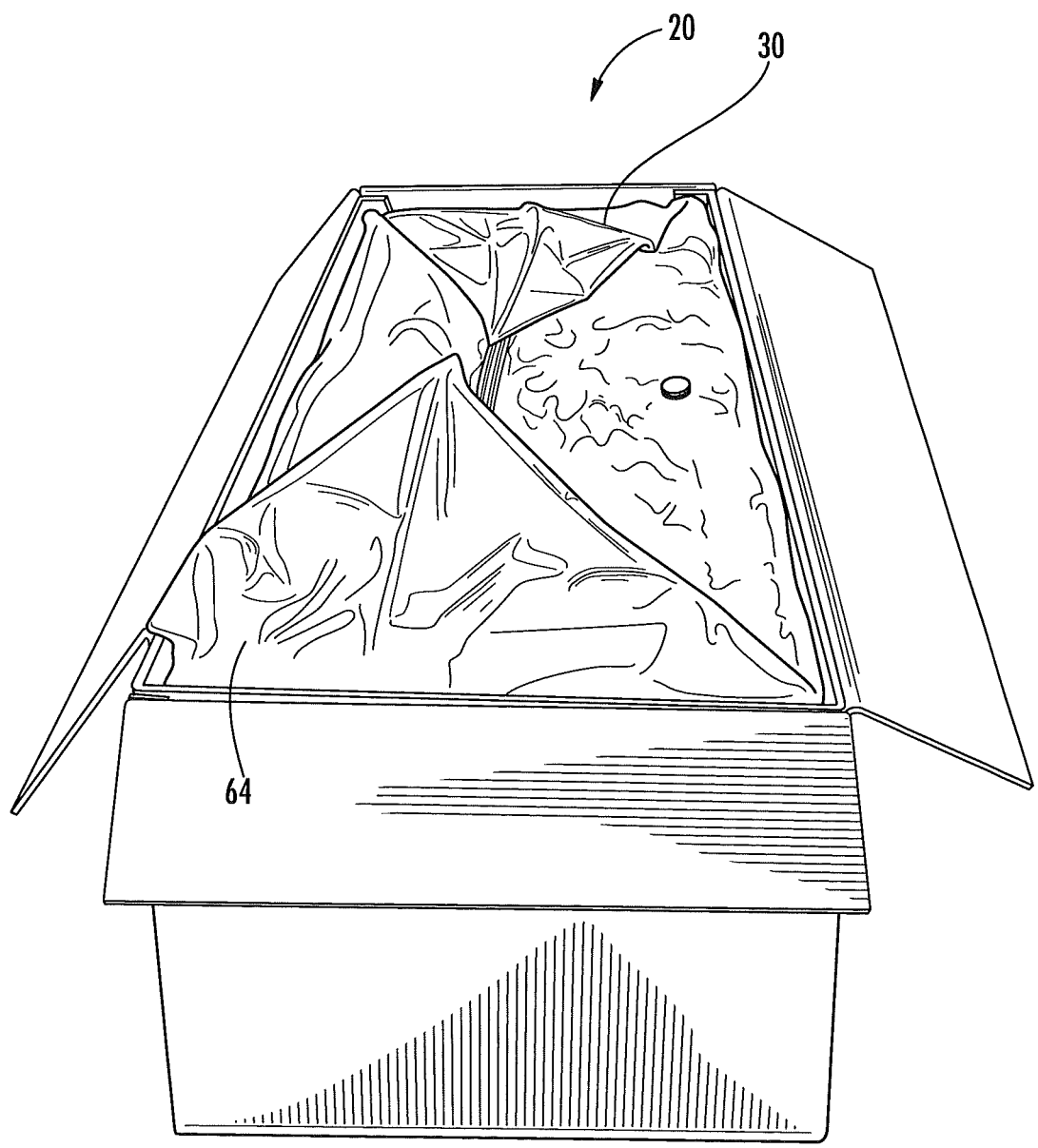
FIG. 9A is a perspective view of a packing container that includes a carton and a flexible bag therein, according to other embodiments of the present invention, after the bag has received a quantity of tobacco therewithin, and after the bag opening has been closed.
Figure 9B:
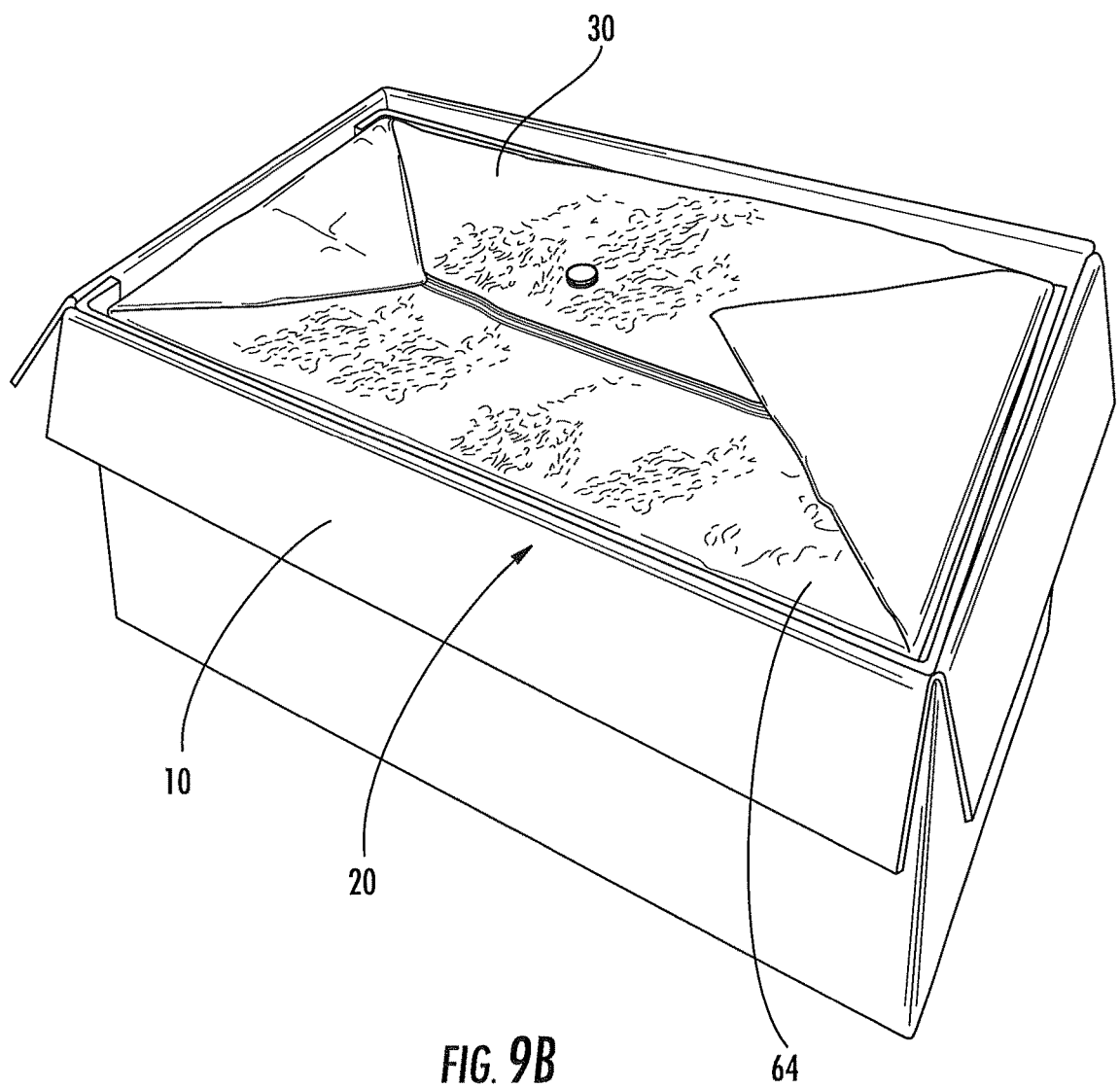
FIG. 9B illustrates the packing container of FIG. 9A after air has been extracted from the bag such that the bag has a sub-atmospheric pressure therein, according to some embodiments of the present invention.

Referring to FIGS. 9A-9B, a packing container 20, according to some embodiments of the present invention, is illustrated. The illustrated bag 30 within the carton 10 is formed from a multi-layer composite having an aluminum layer 64. As illustrated, the aluminum layer completely surrounds the tobacco contents and prohibits any light from reaching the tobacco. The aluminum layer also facilitates detection of the bag 30 within a closed and sealed carton 10, for example, via metal detection equipment, etc. In addition, FIG. 9A illustrates the bag 30 prior to having air extracted from the bag 30. FIG. 9B illustrates the bag 30 of FIG. 9A after air has been extracted from the bag 30 such that the bag 30 has a sub-atmospheric pressure therein.

In other embodiments of the present invention, an opaque or semi-transparent material, other than aluminum may be utilized. For example, a polymeric layer having a color that inhibits light from passing therethrough may be utilized.

Figure 14:
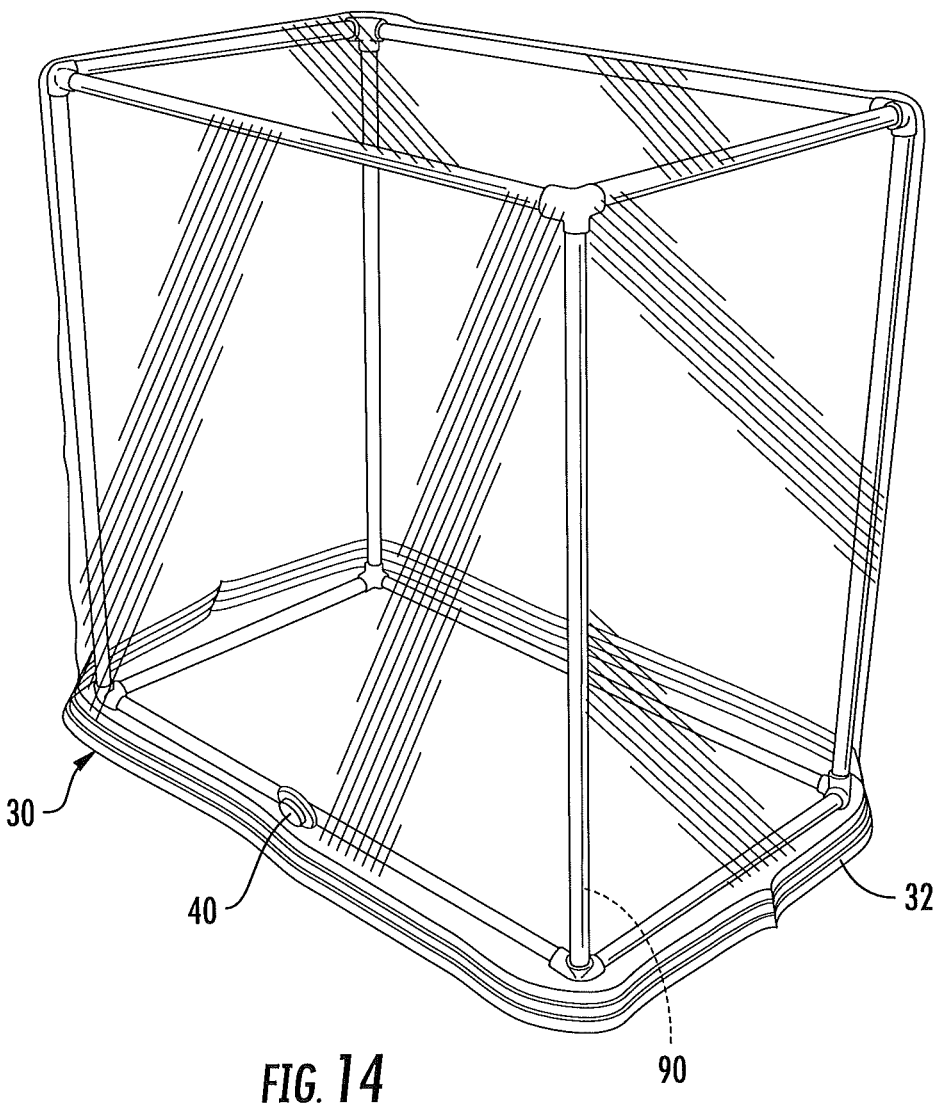
FIG. 14 is a perspective view of an insertion frame that facilitates placement of a flexible, non-porous bag within a carton, according to some embodiments of the present invention.
Figure 15:
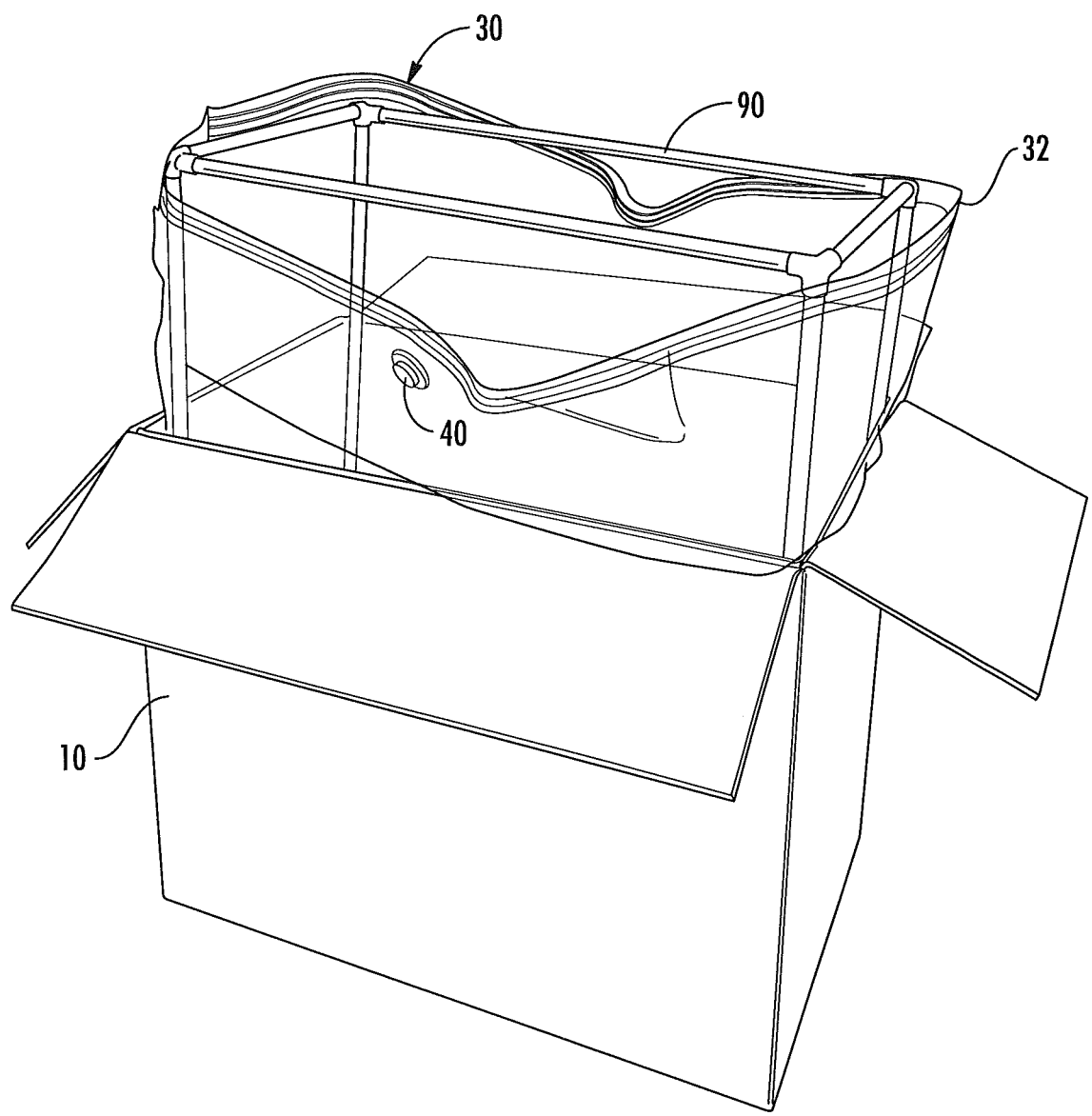
FIG. 15 is a perspective view of a carton receiving a flexible, non-porous bag with the assistance of the insertion frame of FIG. 14.
Figure 16:
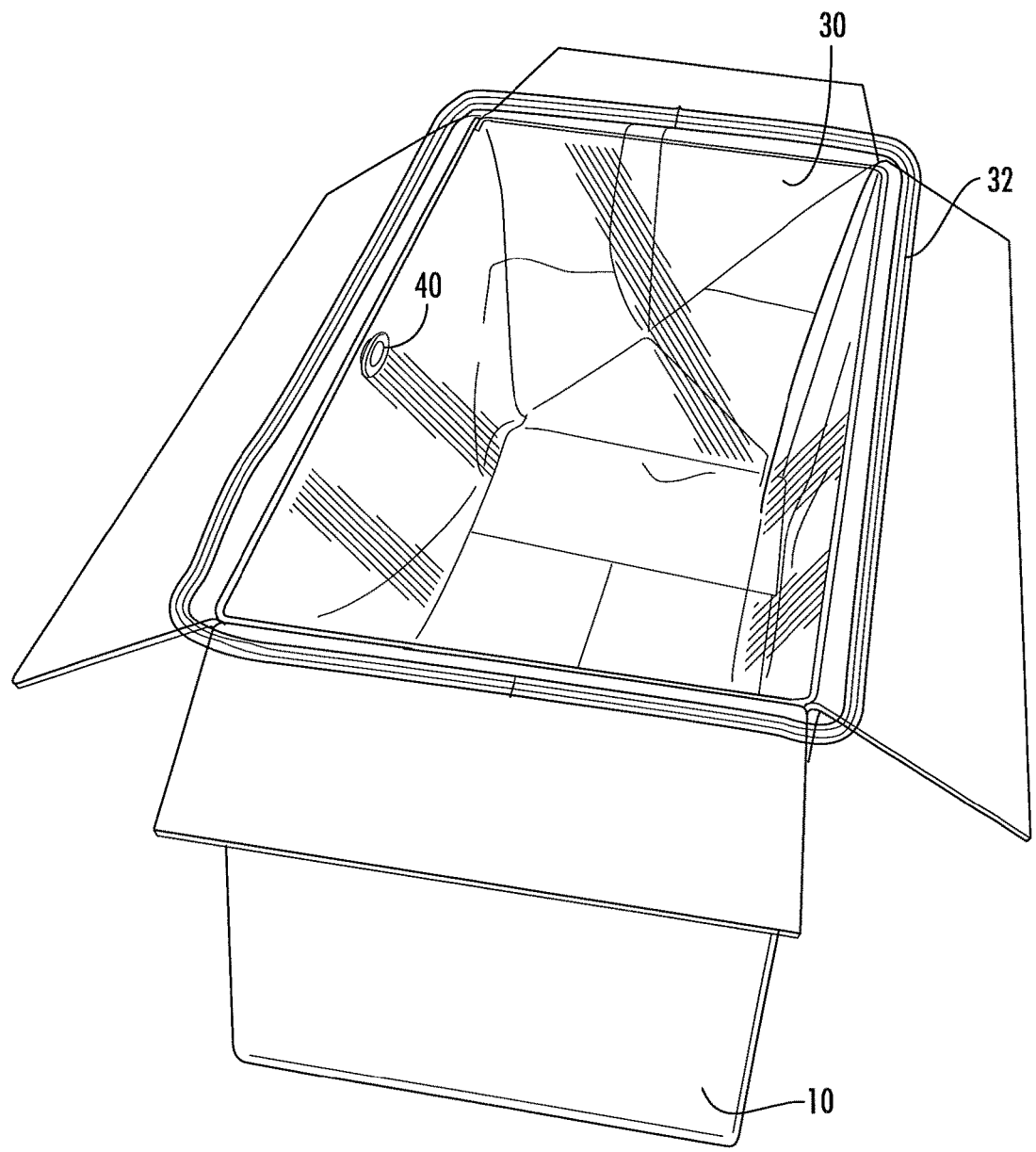
FIG. 16 is a top perspective view of the carton of FIG. 15 with the flexible, non-porous bag received therein and with the insertion frame removed.

Referring to FIGS. 14 and 15, an insertion frame 90 may be utilized to facilitate insertion of flexible, non-porous bags 30 within cartons 10, according to some embodiments of the present invention. The insertion frame 90 allows a bag that is sized to conform with the interior of a carton 10 (thereby reducing extra, unneeded bag material) to be easily and quickly installed within a carton 10. As illustrated in FIG. 14, a bag 30 is initially inserted over the insertion frame 90. The frame 90 and bag 30 assembly is then rotated and inserted within a carton 10, as illustrated in FIG. 15, with the open end of the bag 30 facing outwardly (e.g., upwardly). The frame 90 is then removed from the bag (FIG. 16) prior to tobacco being received within the bag 30.

Figure 10:
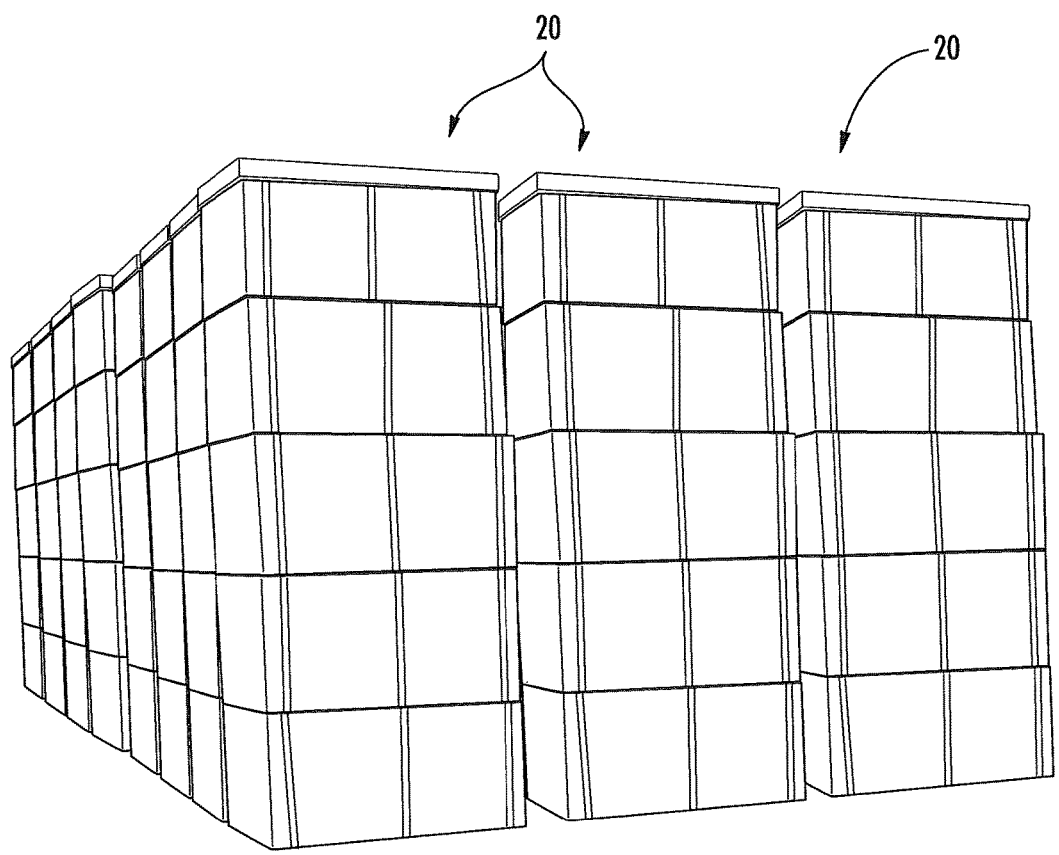
FIG. 10 illustrates a plurality of packing containers in a stacked configuration, according to some embodiments of the present invention.

FIG. 10 illustrates a plurality of packing containers 20, each of which contains a flexible, non-porous bag 30 with a quantity of tightly packed tobacco therewithin, according to embodiments of the present invention. The packing containers 20 are in a stacked configuration. The stacked configuration may be a stored configuration. The stacked configuration may also be a preliminary step to placing the packing containers 20 in a shipping container.

Figure 11:
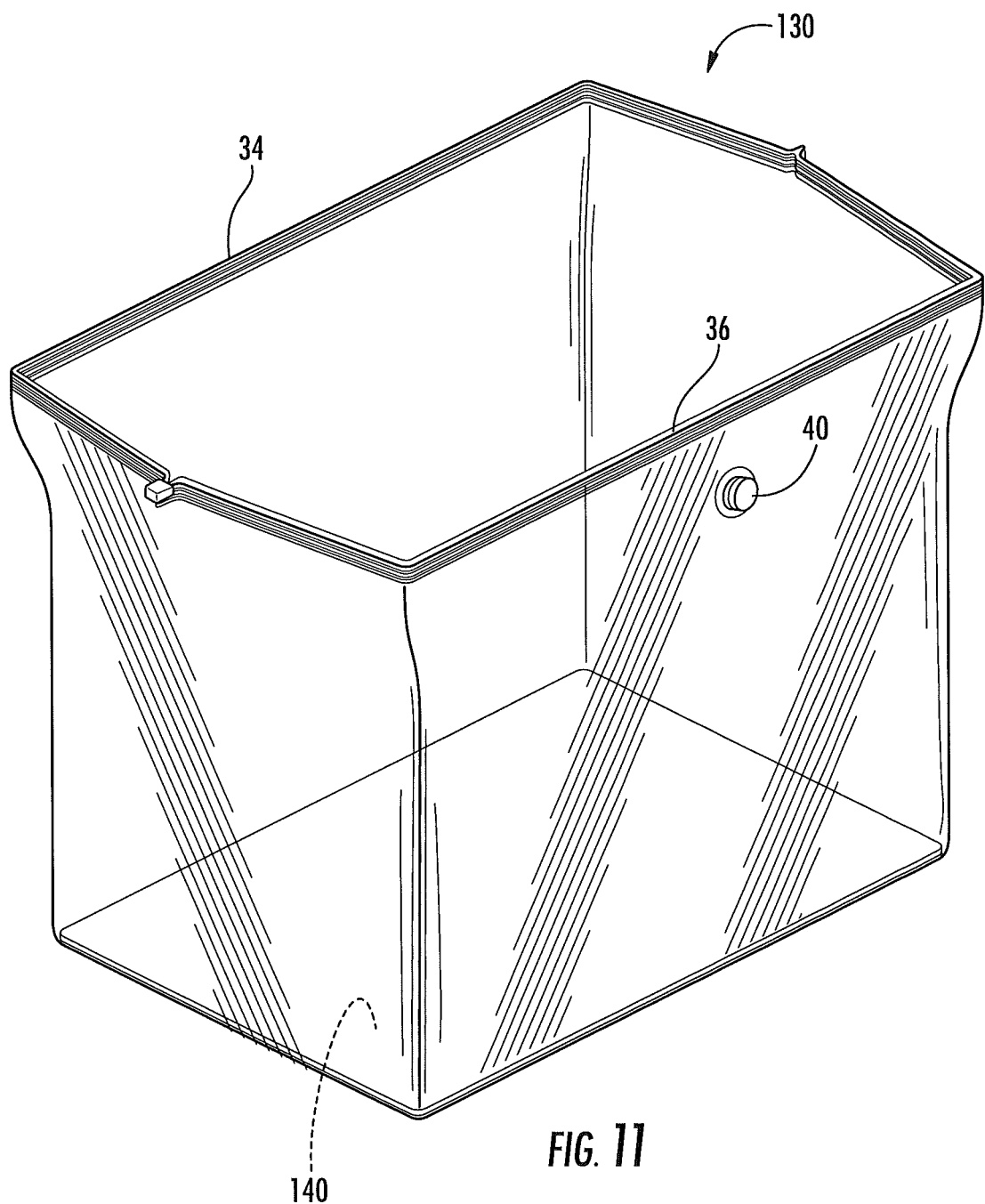
FIG. 11 is a perspective view of a flexible, non-porous bag for receiving tobacco therein, according to some embodiments of the present invention.
Figure 12:
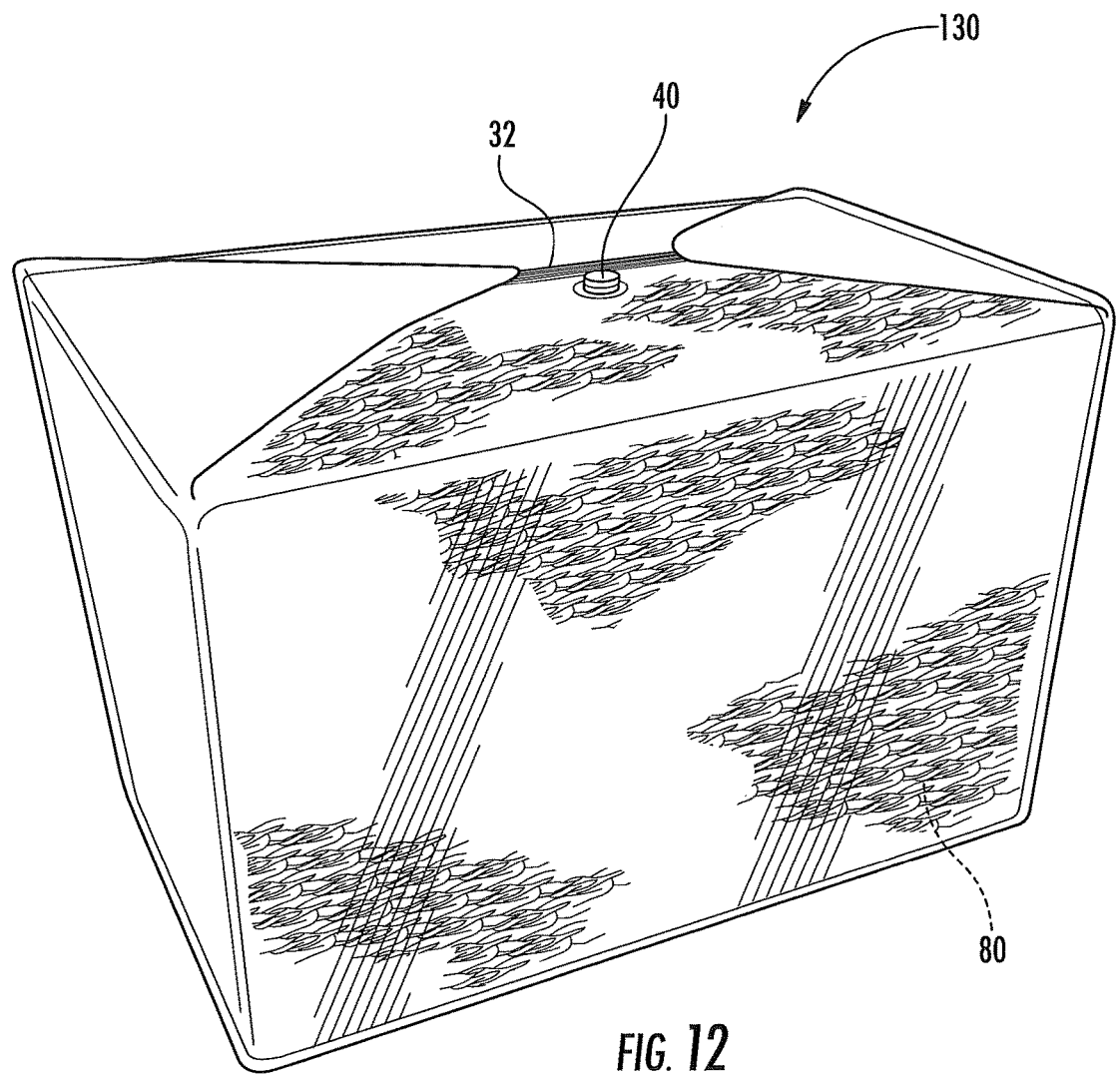
FIG. 12 is a perspective view of the flexible, non-porous bag of FIG. 12 with a quantity of tobacco therewithin and with the bag opening closed.
Figure 13:
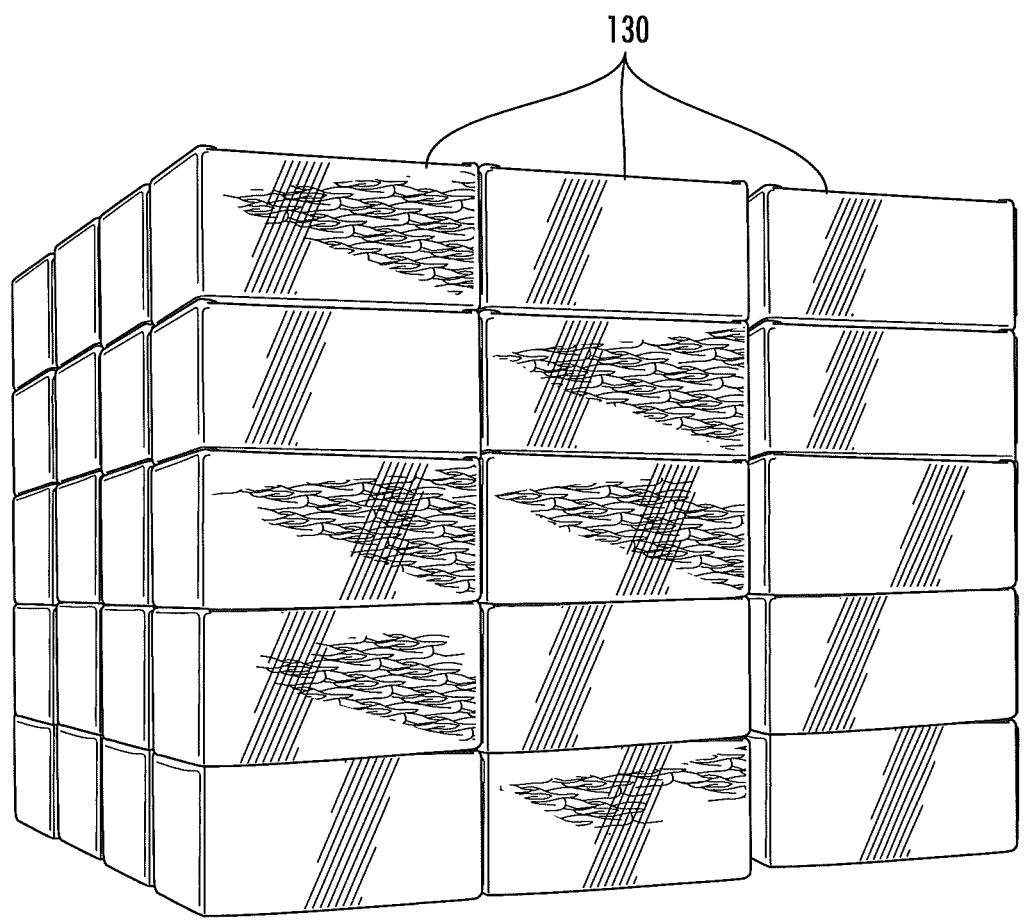
FIG. 13 illustrates a plurality of the flexible, non-porous bags of FIG. 11 containing tobacco and in a stacked configuration, according to some embodiments of the present invention.

According to other embodiments of the present invention, tobacco may be packed, shipped, and/or stored within stand-alone flexible, non-porous bags 130, as illustrated in FIGS. 11-13, without the use of an external carton 10 or other container. Bags 130 of various shapes and configurations may be utilized. Moreover, although not required, such bags 130 may be formed from material having a wall thickness greater than 200 microns in order to withstand potential damage from handling and shipping. In addition, standalone bags 130, according to embodiments of the present invention, are capable of supporting at least between about 15 kilograms and about 240 kilograms of tobacco.

Standalone bags 130, according to embodiments of the present invention, may be formed from an opaque or semi-transparent material, or may be formed from a multi-layered composite material, wherein at least one of the layers is an opaque or semi-transparent material, as described above.

The illustrated standalone non-porous bag 130 includes a closeable opening 32 through which the bag 130 receives a quantity of tightly packed tobacco, as described above. The closeable opening 32 is large enough to allow tobacco packing press equipment to be inserted within a bag 130 to supply a quantity of tobacco. The bag opening 32 is a re-sealable opening that includes a male zipper portion 34 and a corresponding female zipper portion 36 that is configured to matingly engage with the male zipper portion 34, as described above. Although not illustrated, a slide mechanism (e.g., 38, FIG. 6) may be provided that is movably secured to the bag opening 32 and is configured to slide along the bag opening 32 to facilitate engagement of the male and female zipper portions 34, 36 in order to close the bag opening 32 after the bag 130 has been supplied with a quantity of tobacco. The illustrated standalone bag 130 also includes a valve 40 that is utilized for extracting air from the bag 30 after receiving tobacco therein and after the bag opening 32 is sealed closed, as described above. The valve 40 may also be utilized to purge the bag 130, when closed, with an inert gas (e.g., nitrogen, etc.) prior to extracting air from the bag 130.

In some embodiments of the present invention, a standalone bag 130 may include a rigid member 140 disposed within the bag 130 that receives the tobacco thereon. Rigid member 140 can facilitate stacking (FIG. 13) of multiple standalone bags 130 by providing a generally flat surface at the bottom of each standalone bag 130. Moreover, rigid member 140 can provide structural support for a bag 130. Rigid member 140 can have various shapes and configurations, and is not limited to the illustrated configuration.

Flexible non-porous bags 30, 130, 330 according to embodiments of the present invention can be re-used and/or recycled. As such, embodiments of the present invention are environmentally friendly and may reduce costs associated with disposal.

Figure 17:
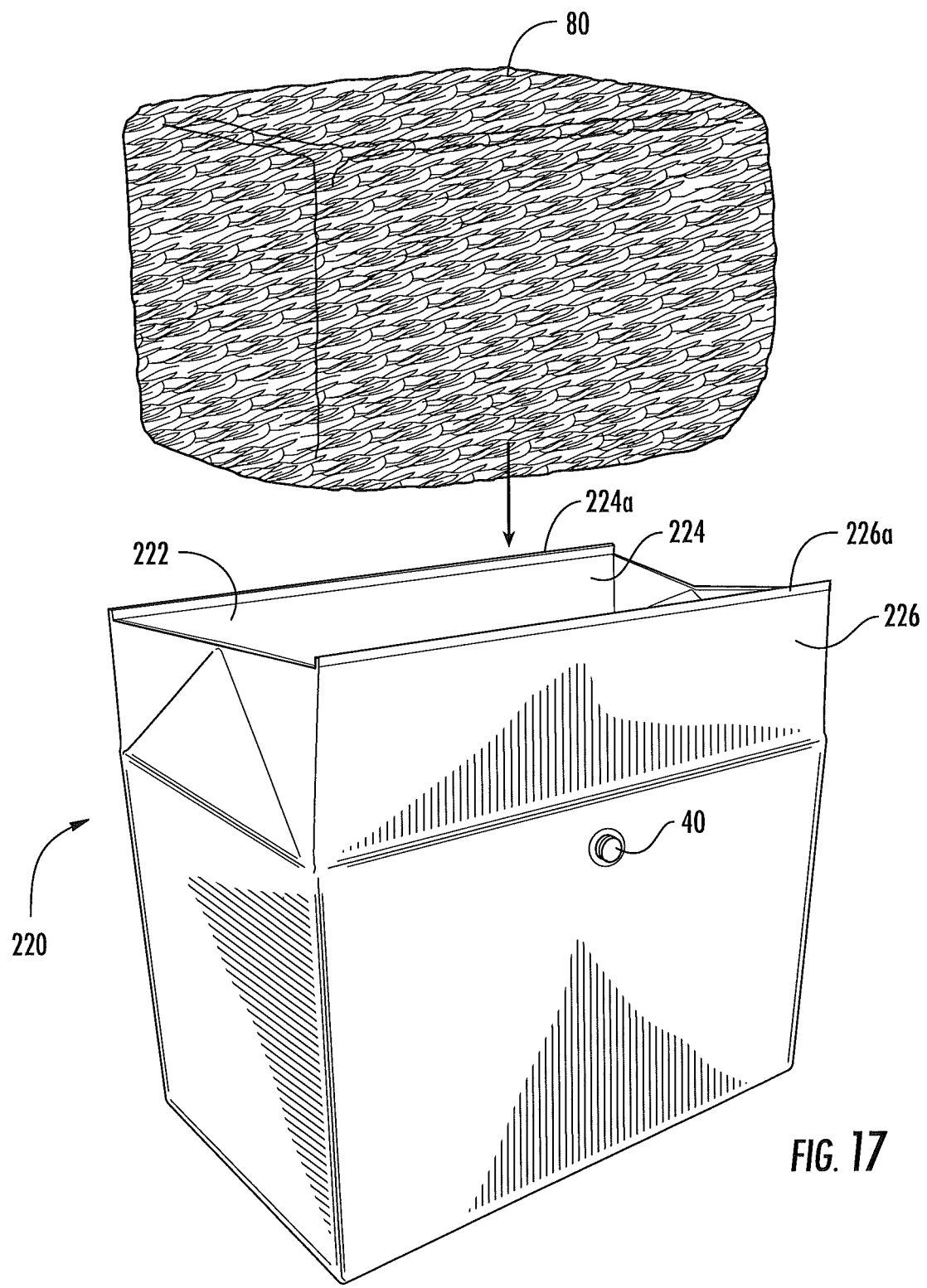
FIG. 17 is a top perspective view of a sealable carton receiving tobacco therein, according to other embodiments of the present invention.
Figure 18:
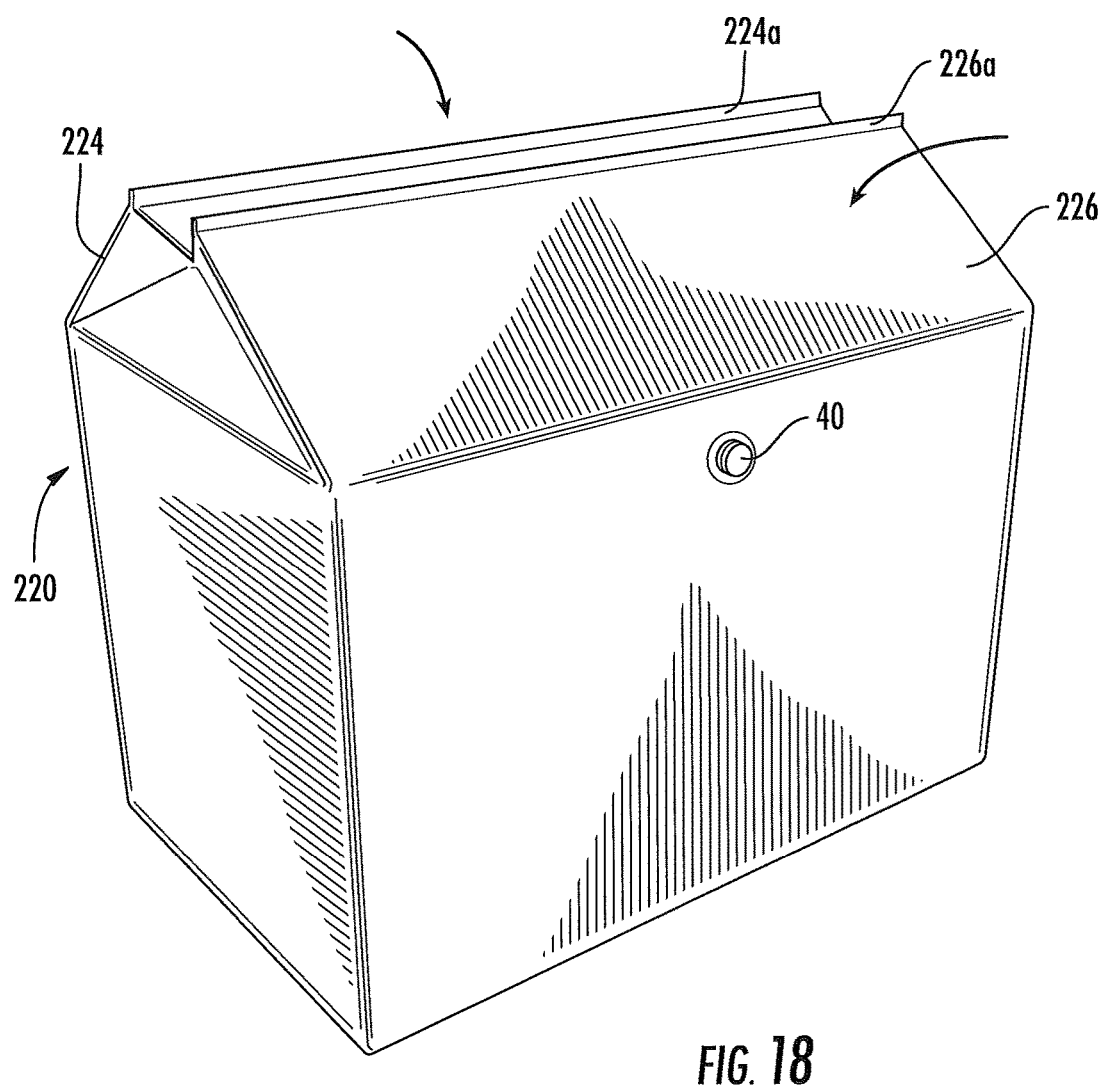
FIG. 18 illustrates the carton of FIG. 17 after receiving tobacco therein, and with the top portions of the carton being closed.
Figure 20:
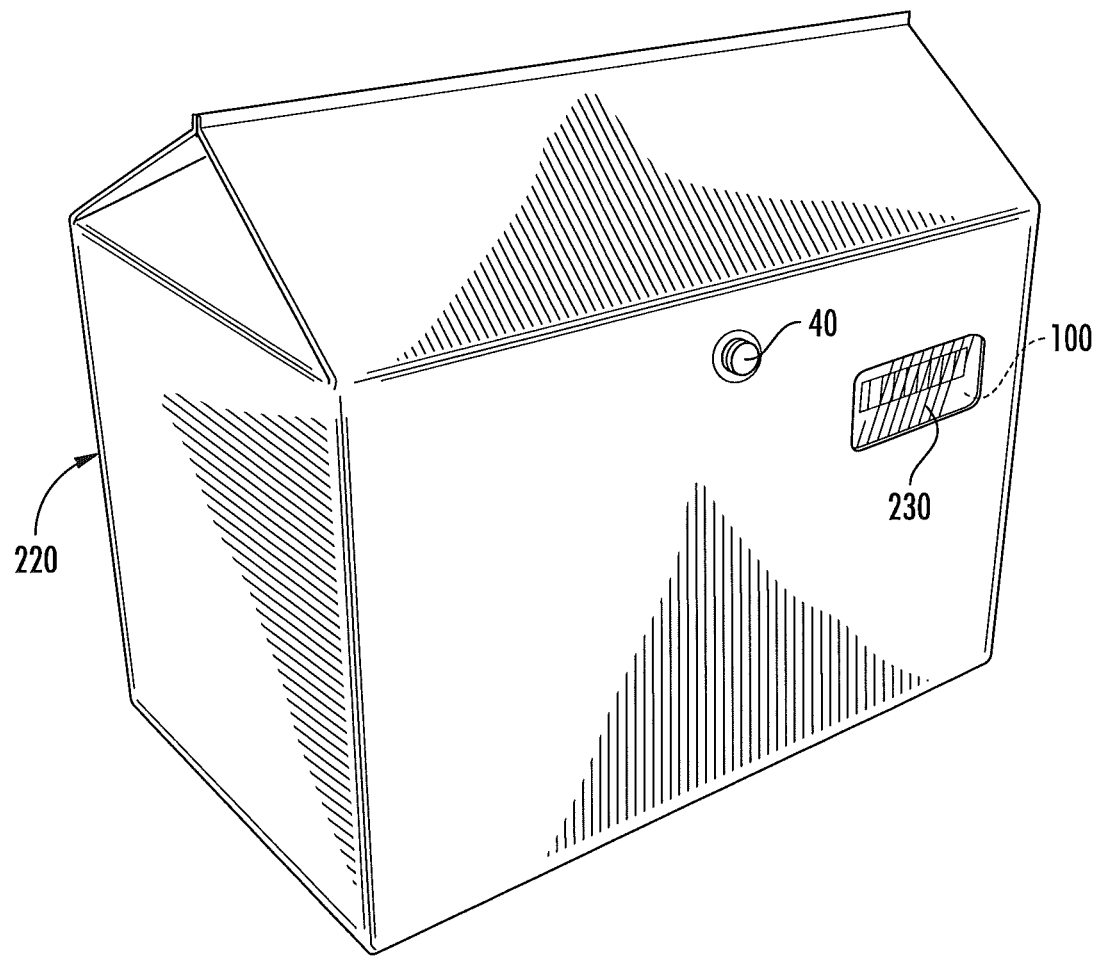
FIG. 20 is a perspective view of a sealable packing carton, according to some embodiments of the present invention, and including a window through which a colorimetric detector is visible.

Referring now to FIGS. 17 and 18, a packing container 220, according to other embodiments of the present invention, is illustrated. The illustrated packing container 220 is a sealable carton that does not require the use of an internal bag (e.g., bag 30, FIG. 5). The container 220 includes a closeable opening 222 through which the container 220 receives a quantity of tightly packed tobacco. In the illustrated embodiment, the container 220 includes opposing upper wall members 224, 226 that are configured to fold together, as illustrated in FIGS. 18 and 20. The edge portions 224a, 226a of respective wall members 224, 226 are configured to be sealed together such that the interior of the container 220 is airtight and can maintain a vacuum therein. In some embodiments, the edge portions 224a, 226a can be sealed together in a fashion similar to that of an aseptic package, such as a milk carton, and such that, once opened after sealing, cannot be resealed together. For example, the edge portions 224a, 226a may be heat sealed together or may be adhesively sealed together. In other embodiments, the edge portions 24a, 226a can have a configuration that allows then to be resealable to facilitate multiple openings and closings thereof.

The packing container 220 is configured to have air extracted therefrom and to maintain a sub-atmospheric pressure therein of, for example, between about 0.10 bar to about 0.70 bar. The illustrated packing container 220 also includes a valve 40, as described above, that is utilized for extracting air from the packing container 220 after receiving tobacco therein and after the packing container 220 is sealed closed. As described above, the valve 40 may be a two-way valve to allow the packing container 220 to be purged with an inert gas (e.g., nitrogen, etc.) prior to extracting air from the packing container 220. However, embodiments of the present invention are not limited to a particular type of valve 40. Various types and shapes of valves may be utilized in accordance with embodiments of the present invention. Moreover, valve 40 can be a one-way valve in some embodiments and a two-way valve in other embodiments.

Figure 19:
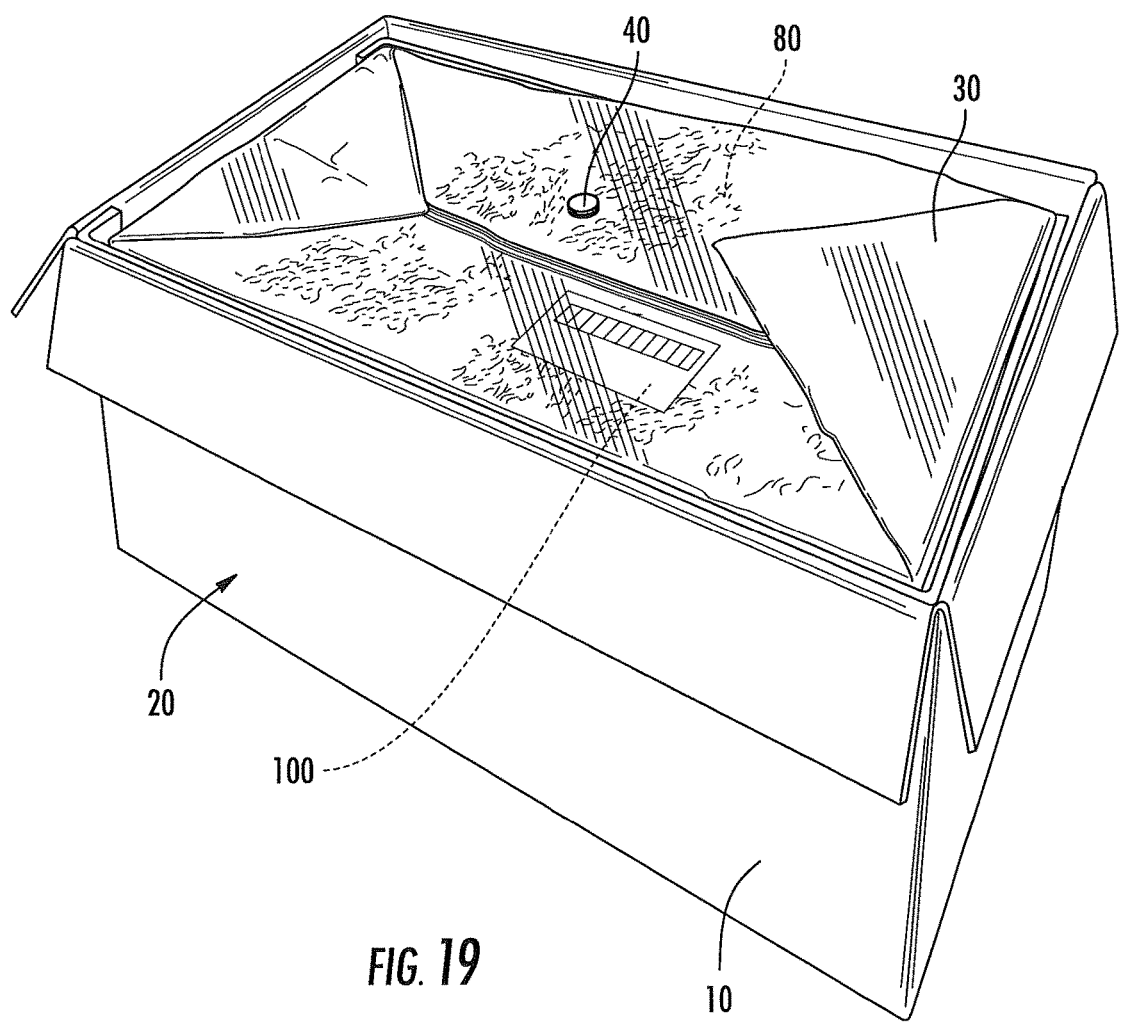
FIG. 19 is a top perspective view of a packing container having a sealed bag containing tobacco within a carton and illustrating a colorimetric detector within the sealed bag, according to some embodiments of the present invention.

Referring to FIG. 19, a packing container 20, according to some embodiments of the present invention, may include a colorimetric detector 100 within an internal bag 30 that is visible upon opening the carton 10. For example, for transparent bags, the colorimetric detector 100 can be viewed through the bag 30, as illustrated in FIG. 19. In other embodiments wherein an internal bag 30 is opaque or semi-transparent, a transparent window may be provided in the bag 30 so as to view a colorimetric detector 100 within the bag 30.

A colorimetric detector 100, according to embodiments of the present invention, includes one or more chemical reagents thereon (e.g., arranged within a display) that, when exposed to in particular environmental conditions and/or chemical elements, visually change color. For example, a chemical reagent may be configured to change color when moisture level (e.g., humidity level) within a sealed bag 30 falls below (or rises above) a predetermined level. Another chemical reagent may be configured to change color when oxygen levels within a sealed bag 30 increase (e.g., indicative of a leak). Chemical reagents may be utilized to measure changes (increases or decreases) in other environmental conditions within a sealed bag 30 including, but not limited to, nitrogen level, carbon-dioxide level, temperature etc.

Another chemical reagent may be configured to change color when a level of a chemical element associated with the tobacco within a sealed bag 30 changes. For example, changes in nitrosamine levels (increases or decreases) within the tobacco may be detected and thereby indicated by a change in reagent color. Changes in the level (increases or decreases) of other tobacco chemicals, such as tobacco leaf sugars and oils may also be detected. Chemical reagents and their use with colorimetric detection are well known and need not be described further herein.

A colorimetric detector 100, according to embodiments of the present invention, may be formed of virtually any material sufficient to retain one or more reagents. In some embodiments, a colorimetric detector 100 may be a piece of paper or other substrate containing one or more reagents. In addition, a colorimetric detector 100, according to embodiments of the present invention, can have various shapes and sizes, without limitation. Embodiments of the present invention are not limited to the illustrated shape or size of the colorimetric detector 100 of FIG. 19. In addition, various indicia (e.g., one or more numerical scales, etc.) may be provided with a colorimetric detector 100 to facilitate quantification of how much change has occurred in a particular condition and/or element. For example, a humidity level scale may be provided to indicate moisture levels (e.g., 10%, 20%, 30%, 40%, 50%, etc.). Other similar scales may be provided for other conditions/elements.

Various types and configurations of colorimetric detectors may be utilized with the various embodiments of the present invention described herein. In addition, colorimetric detectors may be utilized to monitor changes in more than one environmental condition and/or changes in more than one chemical element.

Referring to FIG. 20, a sealable packing container 220, as described above with respect to FIGS. 17 and 18, includes a transparent window 230 through which a colorimetric detector 100 within the sealed packing container 220 can be viewed, according to some embodiments of the present invention. As such, the conditions within the sealed packing container 220 can be viewed from the outside without requiring the sealed container 220 to be opened. As described above, the colorimetric detector 100 can be utilized to detect changes in moisture level, oxygen level, nitrogen level, carbon-dioxide level, temperature, as well as changes in various tobacco leaf chemicals such as nitrosamines, oils and sugars.

According to other embodiments of the present invention, tobacco may be packed, shipped, and/or stored within standalone flexible, non-porous bags 330 having a tubular shape, as illustrated in FIGS. 21-26. Although not required, such bags 330 may be formed from material having a wall thickness greater than 200 microns in order to withstand potential damage from handling and shipping. In addition, standalone bags 330, according to embodiments of the present invention, are capable of supporting at least between about 15 kilograms and about 240 kilograms of tobacco.

Standalone bags 330, according to embodiments of the present invention, may be formed from an opaque or semi-transparent material, or may be formed from a multi-layered composite material, wherein at least one of the layers is an opaque or semi-transparent material, as described above.

Figure 21:
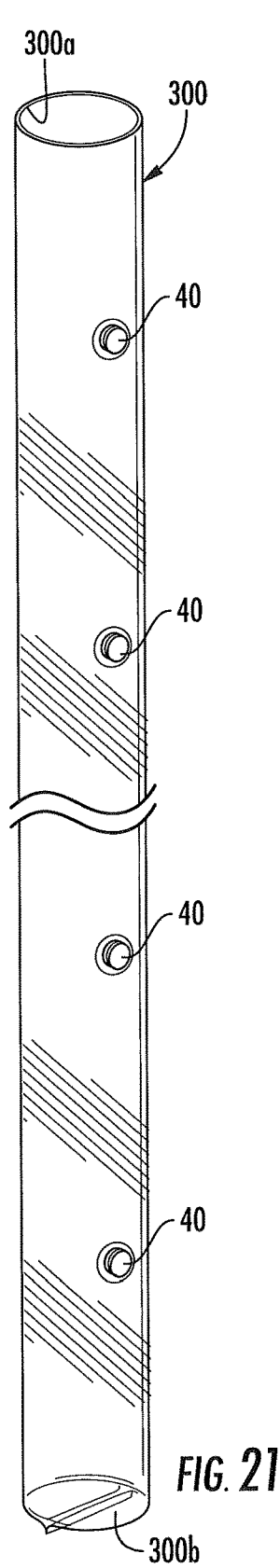
FIGS. 21-25 illustrate operations for packing tobacco within tubular-shaped bags, according to other embodiments of the present invention.
Figure 22:
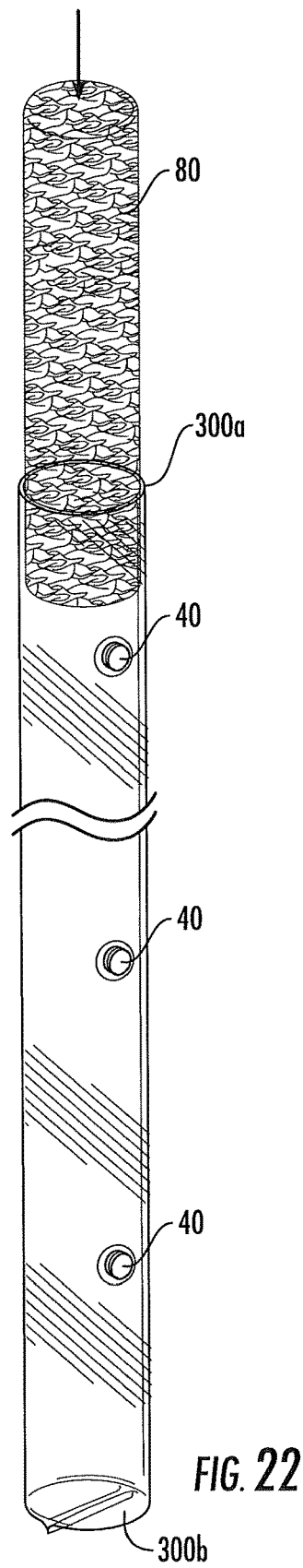
Figure 23:
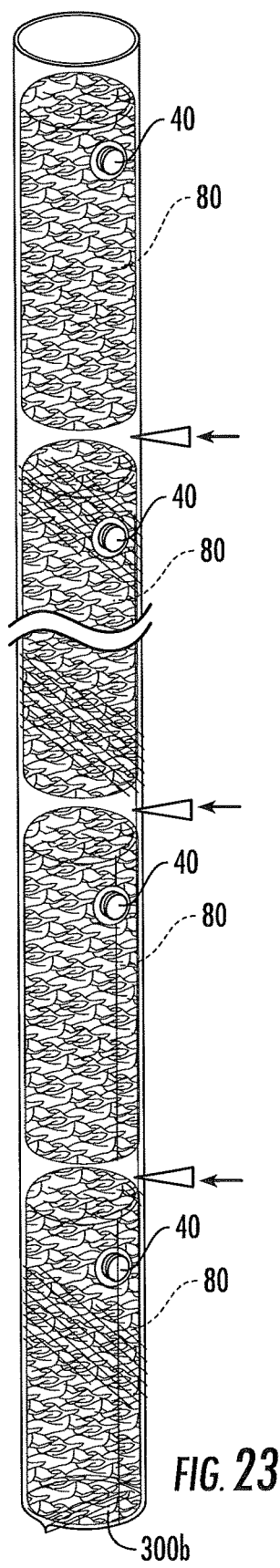
Figures 24, 25, 26:
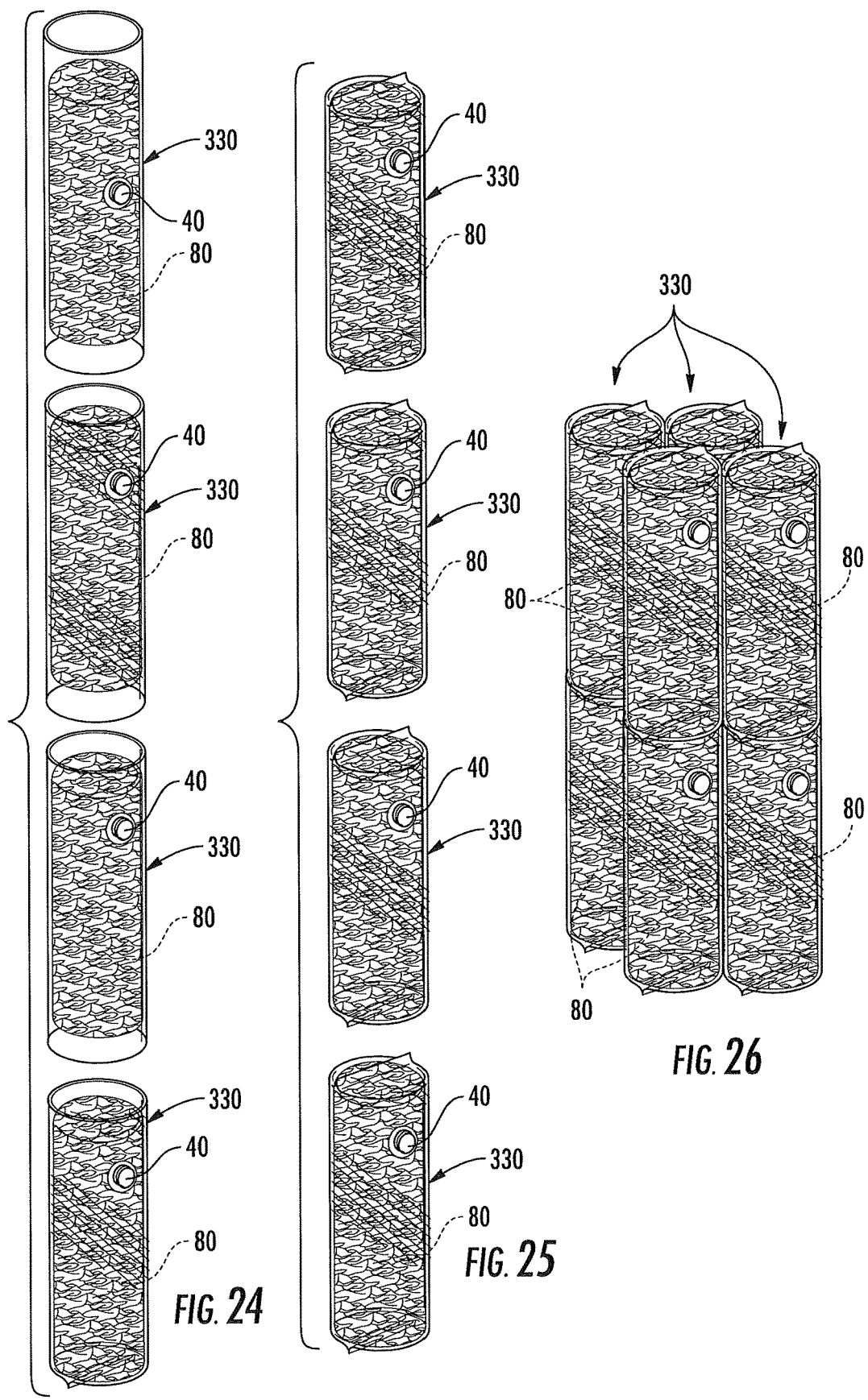
FIG. 26 illustrates a plurality of tubular-shaped bags containing tobacco and in a stacked configuration, according to some embodiments of the present invention.

In one embodiment of the present invention, the standalone non-porous bags 330 are produced by providing an elongated tube 300 having an open first end 300a and an opposite closed end 300b (FIGS. 21-23). The elongated tube 300 is provided with a plurality of valves 40 at predetermined intervals on the elongated tube 300. For example, a valve 40 may be provided every three feet, four feet, or some other constant dimension.

A predetermined amount of tobacco is fed into the elongated tube 300 and the tube 300 is cut in multiple locations, as illustrated in FIG. 23, to produce a plurality of separate tube-shaped bags 330 (FIG. 24). The open ends of the tube-shaped bags 330 are then sealed (e.g., heat sealed). Air is then extracted from each bag 330 via a respective valve 40 to create a sub-atmospheric pressure therein, as described above. The tube-shaped bags 330 can be packed within cartons or may be stacked by themselves.

Tubular shaped bags 330, according to embodiments of the present invention, may be formed and packed with tobacco in various ways. Embodiments of the present invention are not limited to the operations illustrated in FIGS. 21-25.

A colorimetric detector may be utilized with a standalone non-porous bags 330, as described above, to monitor one or more conditions within the sealed bag 330. As described above, a colorimetric detector 100 can be utilized to detect changes in moisture level, oxygen level, nitrogen level, carbon-dioxide level, temperature, as well as changes in various tobacco leaf chemicals such as nitrosamines, oils and sugars.

Figure 27A:
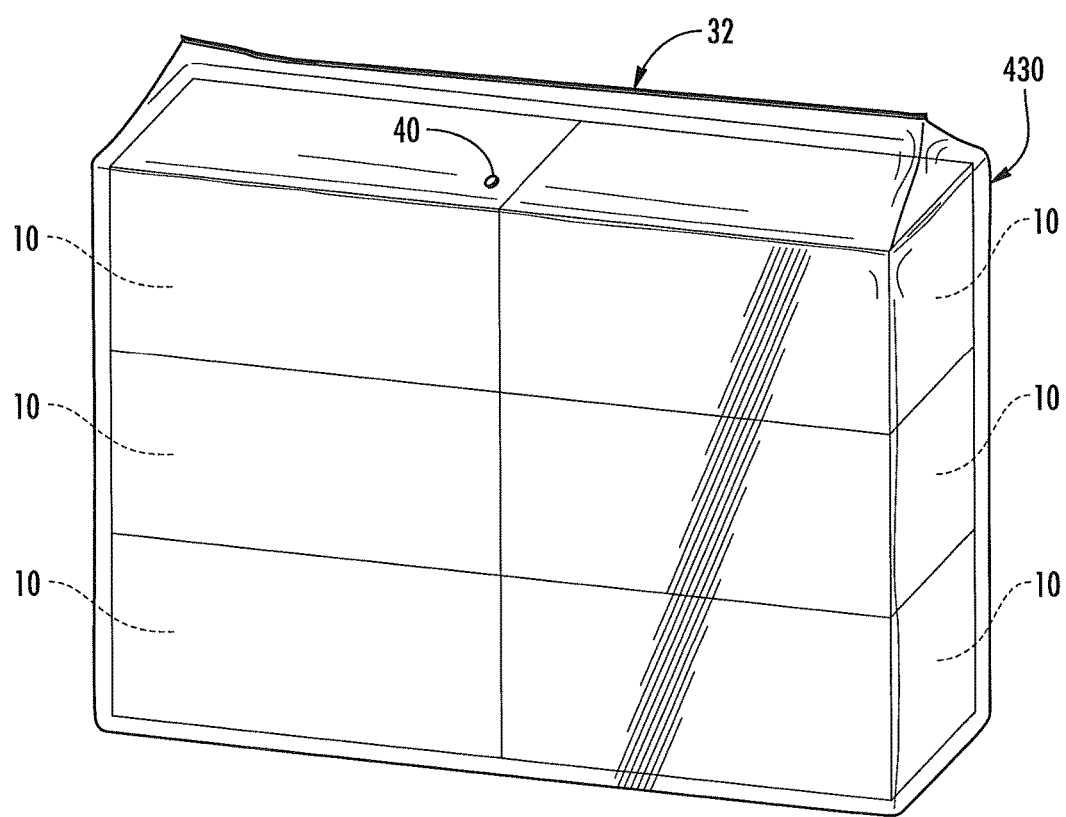
FIG. 27A illustrates a flexible, non-porous bag enclosing multiple cartons of tobacco, according to some embodiments of the present invention, and prior to extracting air therefrom.
Figure 27B:
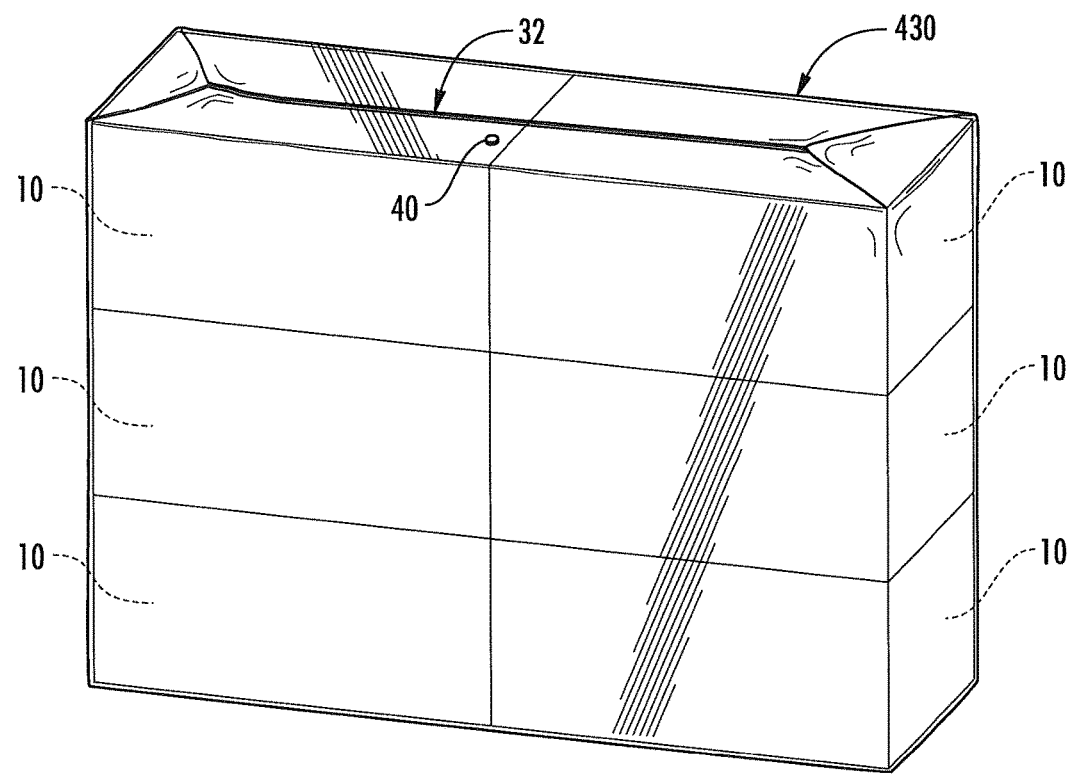
FIG. 27B illustrates the flexible, non-porous bag of FIG. 27A after air has been extracted therefrom.

Referring to FIGS. 27A-27B, a flexible, non-porous bag 430 according to other embodiments of the present invention is illustrated. The bag 430 is configured to enclose multiple containers 10 (e.g., cartons, such as C48, A48 cartons, etc.). In the illustrated embodiment, six (6) cartons 10 are enclosed in the bag 430. However, any number of containers 10 (e.g., 1, 2, 3, 4, 5, 6, or more) may be included within a bag 430. Embodiments of the present invention are not limited to the illustrated six (6) containers 10.

The illustrated bag 430 includes a closeable opening 32 and is configured to have air extracted therefrom and to maintain a sub-atmospheric pressure therein of, for example, between about 0.10 bar to about 0.80 bar. FIG. 27A illustrates the flexible, non-porous bag 430 enclosing multiple cartons 10 of tobacco, with the opening 32 closed, and prior to extracting air from the bag 430. FIG. 27B illustrates the flexible, non-porous bag 430 of FIG. 27A after air has been extracted therefrom.

In some embodiments, the bag opening 32 is a re-sealable opening including a male zipper portion and a corresponding female zipper portion that is configured to matingly engage with the male zipper portion, such as described above.

The flexible, non-porous bag 430 may be formed from a multi-layered composite material with at least one of the layers being an aluminum layer. For example, in some embodiments, the multi-layered composite includes an aluminum layer sandwiched between first and second polymeric layers. In other embodiments, the bag 430 is formed from a multi-layered composite having a polystyrene inner layer, an aluminum middle layer, and a nylon outer layer. In other embodiments, the bag 430 is formed from a semi-transparent or opaque material, or is formed from a multi-layered composite having at least one layer being a semi-transparent or opaque material.

The flexible, non-porous bag 430 may have a wall thickness of at least about 100 microns, and may have a wall thickness between about 100 microns and about 200 microns. According to some embodiments of the present invention, the bag includes a valve 40 that is utilized for extracting air therefrom. The valve 40 may also be utilized to purge the bag, when closed, for example with an inert gas prior to extracting air from the bag 430.

A colorimetric detector may be utilized with a non-porous bags 430, as described above, to monitor one or more conditions within the sealed bag 430. As described above, a colorimetric detector 100 can be utilized to detect changes in moisture level, oxygen level, nitrogen level, carbon-dioxide level, temperature, as well as changes in various tobacco leaf chemicals such as nitrosamines, oils and sugars.

In some embodiments of the present invention, the various bags 30, 130, 330, 430 (as well as carton 220) described above can be formed from material having a color that facilitates identification of the type of tobacco therewithin. Color may also be utilized to indicate destination of the tobacco, origin of the tobacco, ownership of the tobacco, etc.

Packing containers 20 (FIGS. 4-10), 130 (FIGS. 11-13), 220 (FIGS. 17-18), 330 (FIGS. 21-26), 430 (FIGS. 27A-27B) according to embodiments of the present invention have numerous advantages over conventional tobacco shipping/storage cartons. For example, maintaining tobacco under vacuum helps retain the freshness and flavor of the tobacco up to 3 to 5 times longer than in conventional shipping/storage containers. Moreover, maintaining tobacco under vacuum helps prevent loss in moisture content of the tobacco (e.g., preserve the level of moisture of the tobacco at the time of packing) and also prevents mold formation. Because moisture content is maintained, the tobacco leaves retain their color (maintain their "color line") and shape and are less likely to be susceptible to breakage. Thus, sealed bags 30, 130, 330, 430 according to embodiments of the present invention can preserve the particle size distribution (PSD) of the packed tobacco, thereby maintaining the quality and value of the tobacco.

By maintaining the "color line" is meant that the color of the tobacco leaf is retained during shipping and storage. Thus, as a non-limiting example, a tobacco packed with a color line of "lemon" will retain its "lemon" color line and be "lemon" colored when the tobacco reaches its final destination and is opened for further processing. Similarly, a tobacco packed with a color line of, for example, "light orange," "orange," or "mahogany" will retain the respective color line throughout transport and storage in the sealed internal bags 30 according to embodiments of the present invention as compared to tobacco that is packed in a conventional manner.

Sealed bags 30, 130, 330, 430 (and sealed cartons 220) according to embodiments of the present invention also protect tobacco against environmental exposure, including changes of weather conditions (e.g., changes in temperature, changes in humidity, etc.), which can harm tobacco quality. Sealed bags 30, 130, 330, 430 (and sealed cartons 220) also protect tobacco against liquids and odors. In addition, sealed bags 30, 130, 330, 430 (and sealed cartons 220) protect tobacco against sub-zero temperatures that may be encountered in some storage and/or transportation environments.

Another potential benefit resulting from the use of the sealed bags 30, 130, 330, 430 and sealed cartons 220 according to embodiments of the present invention may be the reduction of tobacco-specific nitrosamines (TSNAs). By protecting the tobacco from exposure to environmental changes such as high humidity and/or high temperature as well as exposure to microorganisms (e.g., bacteria, fungi, and the like), the level of TSNAs in the tobacco leaves enclosed in the sealed bags 30, 130, 330, 430 according to embodiments of the present invention may be reduced as compared with tobacco leaves that are not so enclosed.

The sub-atmospheric pressure within a bag 30, 130, 330, 430 (or carton 220) according to embodiments of the present invention lowers the amount of oxygen within the bag which will kill any insects or other pests (e.g., tobacco beetles, tobacco moths, microorganisms, etc.) that may be present in the tobacco. The non-porous nature of the bag material also prevents insects and other pests from finding (i.e., smelling) tobacco therewithin. Thus, the bag material of a bag 30, 130, 330, 430 (and the material of a carton 220) according to embodiments of the present invention provides not only a barrier to insect/pest penetration but also reduces the escape of tobacco odors that attract insects/pests. Because there is reduced risk of insect infestation, there is less need for fumigation of tobacco prior to or during packing, which can result in cost savings.

Further, it is noted that the use of fumigants in tobacco packaging has led to pest populations with increased resistance to those fumigants. Thus, a reduced need for fumigation that may result from the use of sealed bags 30, 130, 330, 430 and cartons 220 according to embodiments of the present invention may also provide the benefit of reducing the level of resistance among the insects and pests that typically infest tobacco.

A further advantage resulting from the use of the sealed bags 30, 130, 330, 430 and cartons 220 according to embodiments of the present invention is the maintenance of the leaf chemistry. Thus, for example, the lower oxygen concentration reduces oxidation of tobacco, thereby preserving tobacco flavors and oils. Therefore, in some embodiments, the level of volatile oil(s) present in the tobacco at the time of packing is preserved. Accordingly, in one embodiment, the level of volatile oil(s) in tobacco packed using the sealed bags 30, 130, 330, 430 and cartons 220 according to embodiments of the present invention is about 100% to about 50% retained as compared to the level of retention of volatile oil(s) in the same tobacco but which has been packed in a conventional manner. In other embodiments, the level of volatile oil(s) in tobacco packed in the sealed bags 30, 130, 330, 430 and cartons 220 according to embodiments of the present invention is retained at about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, or any range therein, or any combination thereof, as compared to the level of retention of volatile oil(s) in the same tobacco but which has been packed in a conventional manner.

In addition, the level of sugars (e.g., reducing sugars) present in the tobacco at the time of packing can also be maintained or preserved through the use of the sealed bags 30, 130, 330, 430 and cartons 220 according to embodiments of the present invention. Non-limiting examples of sugars present in tobacco leaf include sucrose, fructose, glucose, galactose, arabinose, maltose, deoxyribose, mannose, pentose, raffinose, planteose, rhamnose, ribose, xylose, and the like. Thus, in one embodiment, the level of sugars in tobacco packed in the sealed bags 30, 130, 330, 430 and cartons 220 according to embodiments of the present invention is about 100% to about 50% as compared to the level of sugars in the same tobacco that has been packed in a conventional manner. In other embodiments, the level of sugars in tobacco packed in the sealed bags 30, 130, 330, 430 and cartons 220 according to embodiments of the present invention is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, or any range therein, or any combination thereof, as compared to the level of sugars in the same tobacco but which has been packed in a conventional manner. Thus, in one embodiment, tobacco having total reducing sugars of about 20%, when packed in sealed bags 30, 130, 330, 430 and cartons 220 according to embodiments of the present invention, would have total reducing sugars of about 20% when unpacked (i.e., 100% retention) as compared to the level of sugars in the same tobacco but which has been packed in a conventional manner. In other embodiments, tobacco having total reducing sugars of 20%, when packed in sealed bags 30, 130, 330, 430 and cartons 220 according to embodiments of the present invention, would have total reducing sugars of about 20% to about 10% when unpacked (i.e., about 100% to about 50% retention).

The sub-atmospheric pressure within bags 30, 130, 330, 430 and cartons 220 according to embodiments of the present invention also increases, for example, by 20% to 40%, the amount of tobacco that can be packed within a container. As such, packing containers 20, 220 and bags 30, 130, 330, 430 according to embodiments of the present invention can save costs associated with storage and containers. In addition, packing containers, according to embodiments of the present invention, provide an opportunity to ship more tobacco by weight per carton (e.g., per C48 carton), thereby reducing overall freight costs.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A packing container for leaf tobacco, comprising:
    a carton;
    a flexible, non-porous bag located within the carton, wherein the bag comprises a closeable opening through which the bag receives a quantity of tightly packed leaf tobacco, and wherein the bag is configured to have air extracted therefrom and to maintain a sub-atmospheric pressure therein of between 0.10 bar to 0.80 bar; and
    a colorimetric detector positioned within the bag such that the colorimetric detector is viewable through a transparent portion of the bag when closed, and wherein the colorimetric detector is configured to change color when a level of tobacco leaf sugars changes and when a level of tobacco leaf oil changes.

2. The packing container of claim 1, wherein the colorimetric detector is also configured to change color when at least one environmental condition within the bag is outside of a predetermined range, wherein the at least one environmental condition includes oxygen level, nitrogen level, and/or carbon dioxide level, and wherein the colorimetric detector comprises a first portion that is configured to change color when the at least one environmental condition within the bag is outside of the predetermined range and a second portion that is configured to change color when the at least one chemical element associated with the tobacco within the bag is outside of the predetermined range.

3. The packing container of claim 1, wherein the colorimetric detector is also configured to change color when at least one of the following environmental conditions within the bag is outside of a predetermined range: oxygen level, nitrogen level, and/or carbon dioxide level, and when at least one of the following environmental conditions within the bag is outside of a predetermined range: moisture level and/or temperature level.

4. A packing container for leaf tobacco, comprising a flexible, non-porous bag, wherein the bag comprises a closeable opening through which the bag receives a quantity of tightly packed tobacco, wherein the bag is configured to have air extracted therefrom and to maintain a sub-atmospheric pressure therein of between 0.10 bar to 0.80 bar, a colorimetric detector positioned within the bag such that the colorimetric detector is viewable through a transparent portion of the bag when closed, and wherein the colorimetric detector is configured to change color when a level of tobacco leaf sugars changes and when a level of tobacco leaf oil changes, and wherein the bag, when filled with the leaf tobacco, has a shape that allows the bag to be stacked.

5. The packing container of claim 4, wherein the colorimetric detector is also configured to change color when at least one environmental condition within the bag is outside of a predetermined range, wherein the at least one environmental condition includes oxygen level, nitrogen level, and/or carbon dioxide level, and wherein the colorimetric detector comprises a first portion that is configured to change color when the at least one environmental condition within the bag is outside of the predetermined range and a second portion that is configured to change color when the at least one chemical element associated with the tobacco within the bag is outside of the predetermined range.

6. The packing container of claim 4, wherein the bag has an elongated cylindrical shape.

7. The packing container of claim 4, wherein the colorimetric detector is also configured to change color when at least one of the following environmental conditions within the bag is outside of a predetermined range: oxygen level, nitrogen level, and/or carbon dioxide level, and when at least one of the following environmental conditions within the bag is outside of a predetermined range: moisture level and/or temperature level.

8. A packing container for leaf tobacco, comprising a carton having a sealable opening through which the carton receives a quantity of tightly packed leaf tobacco, a colorimetric detector positioned within the carton such that the colorimetric detector is viewable through a window in the carton when closed, wherein the colorimetric detector is configured to change color when a level of tobacco leaf sugars changes and when a level of tobacco leaf oil changes, and wherein the carton is configured to have air extracted therefrom and to maintain a sub-atmospheric pressure therein of between 0.10 bar to 0.80 bar.

9. The packing container of claim 8, wherein the colorimetric detector is also configured to change color when at least one environmental condition within the carton is outside of a predetermined range, wherein the at least one environmental condition includes oxygen level, nitrogen level, and/or carbon dioxide level, and wherein the colorimetric detector comprises a first portion that is configured to change color when the at least one environmental condition within the carton is outside of the predetermined range and a second portion that is configured to change color when the at least one chemical element associated with the tobacco within the carton is outside of the predetermined range.

10. The packing container of claim 8, wherein the carton comprises a valve through which air is extracted from the carton.

11. The packing container of claim 8, wherein the colorimetric detector is also configured to change color when at least one of the following environmental conditions within the carton is outside of a predetermined range: oxygen level, nitrogen level, and/or carbon dioxide level, and when at least one of the following environmental conditions within the carton is outside of a predetermined range: moisture level and/or temperature level.

* * * * *